US008377437B2

(12) United States Patent
Van Lookeren Campagne

(10) Patent No.: US 8,377,437 B2
(45) Date of Patent: Feb. 19, 2013

(54) C3B ANTIBODIES AND METHODS FOR THE PREVENTION AND TREATMENT OF COMPLEMENT-ASSOCIATED DISORDERS

(75) Inventor: Menno Van Lookeren Campagne, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/135,907

(22) Filed: Jul. 18, 2011

(65) Prior Publication Data
US 2012/0128674 A1 May 24, 2012

Related U.S. Application Data

(62) Division of application No. 12/157,073, filed on Jun. 6, 2008, now Pat. No. 8,012,473.

(60) Provisional application No. 61/055,068, filed on May 21, 2008, provisional application No. 60/933,721, filed on Jun. 7, 2007.

(51) Int. Cl.
*A61K 39/395* (2006.01)
*A61K 39/00* (2006.01)

(52) U.S. Cl. ............... 424/130.1; 424/133.1; 424/141.1; 424/142.1; 424/146.1

(58) Field of Classification Search ........................ None
See application file for complete search history.

(56) References Cited

U.S. PATENT DOCUMENTS

| | | | |
|---|---|---|---|
| 4,419,446 A | 12/1983 | Howley | |
| 4,560,655 A | 12/1985 | Baker | |
| 4,601,978 A | 7/1986 | Karin | |
| 4,657,866 A | 4/1987 | Kumar | |
| 4,736,866 A | 4/1988 | Leder | |
| 4,767,704 A | 8/1988 | Cleveland | |
| 4,816,567 A | 3/1989 | Cabilly | |
| 4,873,191 A | 10/1989 | Wagner | |
| 4,927,762 A | 5/1990 | Darfler | |
| 4,965,199 A | 10/1990 | Capon | |
| 5,122,469 A | 6/1992 | Mather | |
| 5,856,135 A | 1/1999 | Tsuchiya et al. | 435/69.3 |
| 6,054,297 A | 4/2000 | Carter | |
| 8,007,798 B2 * | 8/2011 | Ashkenazi et al. | 424/145.1 |
| 2006/0002944 A1 | 1/2006 | Ashkenazi et al. | |
| 2008/0233113 A1 | 9/2008 | Bansal | 424/133.1 |
| 2009/0004183 A1 | 1/2009 | Taylor et al. | 424/133.1 |

FOREIGN PATENT DOCUMENTS

| | | |
|---|---|---|
| EP | 183070 | 10/1985 |
| EP | 244234 | 4/1987 |
| EP | 239400 B1 | 5/1987 |
| EP | 0402226 | 12/1990 |
| EP | 404097 | 12/1990 |
| WO | WO 87/00195 A1 | 1/1987 |
| WO | WO 90/03430 A1 | 4/1990 |
| WO | WO 90/13646 A1 | 11/1990 |
| WO | WO 93/11161 A1 | 6/1993 |
| WO | WO 94/11026 A2 | 5/1994 |
| WO | WO 03/102157 A2 | 12/2003 |
| WO | WO 2006/012621 A | 2/2006 |
| WO | WO 2006/012621 A2 | 2/2006 |

OTHER PUBLICATIONS

Webster's II New Riverside University Dictionary, p. 933, 1984.*
Petmkhin et al, Expert Opin Ther Target 11(5): 625-639, 2007.*
Stryer et al, in Biochemistry, Third edition, W H Freeman Company, New York, pp. 31-33, 1998.*
Ngo et al., 1994, The Protein Folding Problem and Tertiary Structure Prediction, pp. 492-495.*
Yu et al, Investigative Ophthalmology & Visual Science 49(2): 522-527, Feb. 2008.*
Rudikoff et al, Proc Natl Acad Sci USA vol. 79: 1979-1983, 1982.
MacCallum, J. Mol. Biol. 262: 732-745, 1996.
Wu et al, J. Mol. Biol. 294: 151-162, 1999.
Becherer, J. D., et al., "Segment Spanning Residues 727-768 of the Complement C3 Sequence Contains a Neoantigenic Site and Accommodates the Binding of CR1, Factor H, and Factor B," Biochemistry, 31(6): 1787-1794, 1992.
DiLillo, D. J., et al., "Selective and Efficient Inhibition of the Alternative Pathway of Complement by a mAb that Recognizes C3b/iC3b," Molecular Immunology, 43(7): 1010-1019, 2006.
Hack, C., et al., "Disruption of the Internal Thioester Bond in the Third Component of Complement C3 Results in the Exposure of Neodeterminants Also Present on Activation Products of C3 an Analysis with Monoclonal Antibodies," J. of Immunology, 141(5): 1602-1609, 1988.
Mastellos, D., et al., "Novel Monoclonal Antibodies Against Mouse C3 Interfering with Complement Activation: Description of Fine Specificity and Applications to Various Immunoassays," Molecular Immunology, 40(16): 1213-1221, 2004.
Thurman, J. M., et al., "The Central Role of the Alternative Complement Pathway in Human Disease," J. of Immunology, 176(3): 1305-1310, 2006.
Sokoloff, M. H., et al., "Targeting of Cancer Cells with Monoclonal Antibodies Specific for C3b(i)," Cancer Immunology and Immunotherapy, 49(10): 551-562, 2000.
Tosic, L., et al., "Preparation of Monoclonal Antibodies to C3B by Immunization with C3B(I)—Sepharose," J. of Immunological Methods, 120(2): 241-249, 1989.
Wiesmann, C., et al., "Structure of C3b in Complex with CRIg Gives Insights into Regulation of Complement Activation," Nature, 444(7116): 217-220, 2006.
Janssen, B., et al., "Structure of C3b Reveals Conformational Changes that Underlie Complement Activity," Nature, 444(7116): 213-216, 2006.
Ajees, A.A., et al., "The Structure of Complement C3b Provides Insights into Complement C3b Provides Insights into Complement Activation and Regulation," 444(7116): 221-225, 2006.
Steffek, M., et al., "Structural and Binding Studies of C3b in Complex with a Phage Derived Anti-C3 Fab Fragment," J. of Leukocyte Biology Supplement, XP009112631, pp. 28, 2007.
Katschke, Jr., K., et al., "Structural and Functional Analysis of a C3b-Specific Antibody that Selevtively Inhibits the Alternative Pathway of Complement," J. Biol. Chem., XP-002516016, pp. 1-8, 2009.
Aderem, et al., "Mechanisms of phagocytosis in macrophages", Annu. Rev. Immunol., 17:593-623, (1999).
Amit, et al., "Three-dimensional structure of an antigen-antibody complex at 2.8 a resolution", Research Articles, vol. 233, pp. 747-753, (1986).

(Continued)

*Primary Examiner* — Phuong Huynh
(74) *Attorney, Agent, or Firm* — Bonny Yeung; Barrie D. Bell; Arnold & Porter LLP

(57) ABSTRACT

The present invention concerns antibodies to c3b and the prevention and treatment of complement-associated disorder using such antibodies.

14 Claims, 22 Drawing Sheets

OTHER PUBLICATIONS

Anderson, et al., "A role for local inflammation in the formation of drusen in the aging eye", American Journal of Ophthalmology, vol. 134, No. 3, pp. 411-431, (2002).

Auchincloss, et al., "Transplantation and graft rejection", Fundamental Immunology, Chapter 33, pp. 889-922, (1989).

Banda, et al., "Prevention of collagen-induced arthritis in mice transgenic for the complement inhibitor complement receptor 1-related gene/protein", The journal of Immunology, pp. 2109-2115, (2003).

Barnes, et al., "Methods for growth of cultured cells in serum-free medium", Analytical Biochemistry, 102: 255-270, (1980).

Bolton, et al., "Recent advances in the pharmacological control of experimental allergic encephalomyelitis (EAE) and the implications for multiple sclerosis treatment", Pharmacological control of EAE, 1:143-149, (1995).

Brown, et al., "Complement receptors, adhesion and phagocytosis", Infectious agents and disease, 1:63-70, (1992).

Bruijn, et al., "Human complement component C3: cDNA coding sequence and derived primary structure", Proc. Natl. Acad. Sci., vol. 82, pp. 708-712, (1985).

Carroll, et al., "The complement system in regulation of adaptive immunity", Nature Immunology, vol. 5, No. 10, pp. 981-986,(2004).

Carter, et al., "High level *Escherichia coli* expression and production of a bivalent humanized antibody fragment", Biotechnology, vol. 10, pp. 163-167, (1992).

Carter, et al., "Humanization of an anti-p185her2 antibody for human cancer therapy", Proc. Natl. Acad Sci., vol. 89, pp. 4285-4289, (1992).

Champe, et al., "Monoclonal antibodies that block the activity of leukocyte function-associated antigen 1 recognize three discrete epitopes in the inserted doman of CD11a", The journal of biological chemistry, vol. 270, pp. 1388-1394, (1995).

Chothia, et al., "Canonical structures for the hypervariable regions of immunoglobulins", J. Mol. Biol., 196:901-917, (1987).

Clackson, et al., "Making antibody fragments using phage display libraries", Letters to Nature, vol. 352, pp. 624-628, (1991).

Connolly, et al., "Analytical molecular surface calculation", J. Appl. Cryst., 16:548-558, (1983).

Cunningham, et al., "High-resolution epitope mapping of hGH-receptor interactions by alanine-scanning mutagenesis", Science Reports, vol. 244, pp. 1081-1085, (1989).

Donoso, et al., "The role of inflammation in the pathogenesis of age-related macular degeneration", Survey of Ophthalmology, vol. 51, No. 2, pp. 137-152, (2006).

Duncan, et al., "Repair of myelin disease: strategies and progress in animal models", Molecular Medicine Today, pp. 554-561, (1997).

Eigenbrot, et al., "X-ray structures of the antigen-binding domains from three variants of humanized anti-p185her2 antibody 4d5 and comparison with molecular modeling", J. Mol. Biol., 229:969-995, (1993).

Fleer, et al., "Stable multicopy vectors for high-level secretion of recombinant human serum albumin by *Kluyveromyces* yeasts", Biotechnology, vol. 9, pp. 968-975, (1991).

Garrard, et al., "Selection of an anti-IGT-1 from a Fab phage library created by mutagenesis of multiple CDR loops", Gene, 128:103-109, (1993).

Gold, et al., "Variation in factor B (BF) and complement component 2 (C2) genes is associated with age-related macular degeneration", Nature Genetics, vol. 38, No. 4, pp. 458-462, (2006).

Grabbe, et al., "Immunoregulatory mechanisms involved in elicitation of allergic contact hypersensitivity", Immunology Today, vol. 19, No. 1, pp. 37-44, (1998).

Graham, et al., "Characteristics of a human cell line transformed by DNA from human adenovirus type 5", J. gen. Virol., 36: 59-72, (1977).

Guss, et al., "Structure of the IgG-binding regions of streptococcal protein G", The EMBO Journal, vol. 5, No. 7, pp. 1567-1575, (1986).

Hageman, et al., "A common haplotype in the complement regulatory gene factor H (HFI/CFH) predisposes individuals to age-related macular degeneration", PNAS, vol. 102, No. 20, pp. 7227-7232, (2005).

Hageman, et al., "An integrated hypothesis that considers drusen as biomarkers of immune-mediated processes at the RPE-Bruch's membrane interface in aging and age-related macular degeneration", Progress in retinal and eye research, vol. 20, No. 6, pp. 705,732, (2001).

Hageman, et al., "Extended haplotypes in the complement factor H (CFH) and CFH-related (CFHR) family of genes protect against age-related macular degeneration: Characterization, ethnic distribution and evolutionary implications", Annals of Medicine, 38:592-604, (2006).

Holers, et al., "The evolution of mouse and human complement C3-binding proteins: divergence of form but conservation of function", Immunology Today, vol. 13, No. 6, pp. 231-236,(1992).

Holliger, et al., "Diabodies: Small bivalent and bispecific antibody fragments", Proc. Natl. Acad. Sci., vol. 90, pp. 6444-6448, (1993).

Hourcade, et al., "The regulators of complement activation (RCA) gene cluster", Advances in Immunology, vol. 45, pp. 381-416, (1989).

Janssen, et al., "Structural insights into the central complement component C3", Molecular Immunology, 44:3-10, (2007).

Jones, et al., "Proteinase mutants of *Saccharomyces cerevisiae*", Genetics, 85:23-33, (1977).

Jones, et al., "Replacing the complementarity-determining regions in a human antibody with those from a mouse", Letters to Nature, vol. 321, pp. 522-525, (1986).

Kenealy, et al., "Linkage analysis for age-related macular degeneration supports a gene on chromosome 10q26", pp. 1-10, (2004).

Klein, et al., "Age-related macular degeneration", Arch Ophthalmol, vol. 116, pp. 1082-1088, (1998).

Klein, et al., "Complement factor H polymorphism in age-related macular degeneration", Research Articles, vol. 308, pp. 385-389, (2005).

Knappik, et al., "Fully synthetic human combinatorial antibody libraries (HuCAL) based on modular consensus frameworks and CDRs randomized with Trinucleotides", J.M.B., 296:57-86, (2000).

Kniazeva, et al., "A new locus for dominant drusen and macular degeneration maps to chromosome 6q14", American journal of Ophthalmology, 130:197-202, (2000).

Kohler, et al., "Continuous cultures of fused cells secreting antibody of predefined specificity", Nature, vol. 256, pp. 495-497, (1975).

Kunkel, et al., "Rapid and efficient site-specific mutagenesis without phenotypic selection", Proc. Natl Acad., vol. 82, pp. 488-492, (1985).

Lavitrano, et al., "Sperm cells as vectors for introducing foreign DNA into eggs: Genetic transformation of mice", Cell, vol. 57, pp. 717-723, (1989).

Lechner, et al., "Characterization of strand displacement synthesis catalyzed by bacteriophage T7 DNA polymerase", The journal of biological chemistry, vol. 258, No. 18, pp. 11174-11184, (1983).

Lee, et al., "The interpretation of protein structures: Estimation of static accessibility", J. mol. Biol., 55:379-400, (1971).

Lee, et al., "High-affinity human antibodies from phage-displayed synthetic fab libraries with a single framework scaffold", JMB, 340:1073-1093, (2004).

Lindmark, et al., "Binding of immunoglobulins to protein A and immunoglobulin levels in mammalian sera", Journal of immunological methods, 62:1-13, (1983).

Lo, et al., "Transformation by iontophoretic microinjection of DNA: multiple integrations without tandem insertions", Molecular and cellular biology, vol. 3, No. 10, pp. 1803-1814, (1983).

Lowman, et al., "Monovalent phage display: A method for selecting variant proteins from random libraries", Methods: A companion to methods in Enzymology, vol. 3, No. 3, pp. 205-216, (1991).

Lutz, et al., "Complement amplification revisited", Molecular Immunology, 43: 2-12, (2006).

Lyengar, et al., "Dissection of genomewide-scan data in extended families reveals a major locus and oligogenic susceptibility for age-related macular degeneration", Am. J. Genet., 74: 20-39, (2004).

Majewski, et al., "Age-related macular degeneration—a genome scan in extended families", Am. J. Genet., 73: 540-550, (2003).

Marasco, et al., "Design, intracellular expression, and activity of a human anti-human immunodeficiency virus type 1 gp120 single-chain antibody", Proc. Natl. Acad. Sci., vol. 90, pp. 7889-7893, (1993).

Marks, et al., "Human antibodies from v-gene libraries displayed on phage", JMB, 222: 581-597, (1991).
Mather, et al., "Culture of testicular cells in hormone-supplemented serum-free medium", Annals New York Academy of Sciences, pp. 44-68, (1982).
Mather, et al., "Establishment and characterization of two distinct mouse testicular epithelial cell lines", Biology Reproduction, 23: 243-252, (1980).
Mollnes, et al., "Complement in inflammatory tissue damage and disease", Trends in Immunology, vol. 23, No. 2, pp. 61-64, (2002).
Morgan, et al., "Complement therapeutics: history and current progress", Molecular Immunology, 40:159-170, (2003).
Morrison, et al., "Chimeric human antibody molecules: mouse antigen-binding domains with human constant region domains", Proc. Natl. Acad., vol. 81, pp. 6851-6855, (1984).
Nickoloff, et al., "Severe combined immunodeficiency mouse and human psoriatic skin chimeras", American journal of pathology, vol. 146, No. 3, pp. 580-588, (1995).
Oglesby, et al., "Membrane cofactor protein (CD46) protects cells from complement-mediated attack by an intrinsic mechanism", J. Exp. Med., vol. 175, pp. 1547-1551, (1992).
Pacios, et al., "Arvolmol/Contour: Molecular surface areas and volumes on personal computers", Computers Chem., vol. 18, No. 4, pp. 377-385, (1994).
Presta, "Antibody engineering", Current opinion in structure biology, 2:593-596, (1992).
Presta, et al., "Humanization of an anti-vascular endothelial growth factor monoclonal antibody for the therapy of solid tumors and other disorders", Cancer Research, 57:4593-4599, (1997).
Pyz, et al., "C-type lectin-like receptors on myeloid cells", Annals of Medicine, 38:242-251, (2006).
Rawal, et al., "Formation of high-affinity c5 convertases of the alternative pathway of complement", The journal of immunology, 166:2635-2642, (2001).
Reyes, et al., "Expression of human β-interferon cDNA under the control of a thymidine kinase promoter from herpes simplex virus", Nature, vol. 297, pp. 598-601, (1982).
Riechmann, et al., "Reshaping human antibodies for therapy", Nature Articles, vol. 332, pp. 323-327, (1988).
Seddon, et al., "A genomewide scan for age-related macular degeneration provides evidence for linkage to several chromosomal regions", Am. J. Hum. Genet., 73:780-790, (2003).
Schick, et al., "A whole-genome screen of a quantitative trait of age-related maculopathy in sibships from the dam eye study", Am. J. Hum. Genet., 72:1412-1424, (2003).
Schon, et al., "Animal models of psoriasis—what can we learn from them?", The journal of investigative dermatology, pp. 405-410, (1999).
Schon, et al., "Murine psoriasis-like disorder induced by naïve CD4 T cells", Nature Medicine, vol. 3, No. 2, pp. 183-188, (1997).
Sidhu, et al., "Phage display for selection of novel binding peptides", Methods in Enzymology, vol. 328, pp. 333-363, (2000).
Stinchcomb, et al., "Isolation and characterization of a yeast chromosomal replicator", Nature, vol. 282, pp. 39-43, (1979).
Stuart, et al., "Phagocytosis: Elegant complexity", Immunity, vol. 22, pp. 539-550, (2005).
Tanabe, et al., "Combined immunosuppressive therapy with low dose FK506 and antimetabolites in rat allogeneic heart transplantation", Transplantation, vol. 58, pp. 23-27, (1994).
Taylor, et al., "Macrophage receptors and immune recognition", Annu. Rev. Immunol., 23:901-944, (2005).
Taylor, et al., "Pattern recognition receptors and differentiation antigens define murine myeloid cell heterogeneity ex vivo", Eur. J. Immunol., 33:2090-2097, (2003).
Terato, et al., "Collagen-induced arthritis in mice: Synergistic effect of E. coli lipopolysaccharide bypasses epitope specificity in the induction of arthritis with monoclonal antibodies to type II collagen", Autoimmunity, vol. 22, pp. 137-147, (1995).
Terato, et al., "Induction of arthritis with monoclonal antibodies to collagen", Monoclonal antibody-induced arthritis, vol. 148, pp. 2103-2108, (1992).
Terato, et al., "Induction of chronic autoimmune arthritis in dba/1 mice by oral administration of type II collagen and Escherichia coli lipopolysaccharide", British journal of Rheumatology, 35:828-838, (1996).
Thompson, et al., "Germ line transmission and expression of a corrected HPRT gene produced by gene targeting in embryonic stem cells", Cell, vol. 56, pp. 313-321, (1989).
Thurman, et al., "The central role of the alternative complement pathway in human disease", Journal of Immunology, pp. 1305-1310, (2005).
Tinubu, et al., "Humanized antibody directed to the IL-2 receptor β-chain prolongs primate cardiac allograft survival", The journal of immunology, 153:4330-4338, (1994).
Underhill, et al., "Phagocytosis of microbes: Complexity in action", Annu. Rev. Immunol., 20:825-852, (2002).
Urlaub, et al., "Isolation of Chinese hamster cell mutants deficient in dihydrofolate reductase activity", Proc. Natl. Acad., vol. 77, pp. 4216-4220,(1980).
Van der berg, et al., "*Kluveromyces* as a host for heterologous gene expression: expression and secretion of prochymosin", Biotechnology, vol. 8, pp. 135-139, (1990).
Van der berg, et al., "Efficient insertion of genes into the mouse germ line via retroviral vectors", Proc. Natl. Acad., vol. 82, pp. 6148-6152, (1985).
Weeks, et al., "Age-related maculopathy: An expanded genome-wide scan with evidence of susceptibility loci within the 1q31 and 17q25 regions", Age-related maculopathy, vol. 132, No. 5, pp. 682-692, (2001).
Weisman, et al., "Soluble human complement receptor type 1: in vivo inhibitor of complement suppressing post-ischemic myocardial inflammation and necrosis", Science, vol. 249, pp. 146-151, (1990).
Walport, et al., "Advances in Immunology", The New England journal of medicine, vol. 344, No. 14, pp. 1058-1066, (2001).
Wolyniec, et al., "Reduction of antigen-induced airway hyperreactivity and eosinophilia in ICAM-1-deficient mice", Am. J. Respir. Cell Mol. Biol., vol. 18, pp. 777-785, (1998).
Yaniv, et al., "Enhancing elements for activation of eukaryotic promoters", Nature, vol. 297, pp. 17-18, (1982).
Zapata, et al., "Engineering linear F(ab')2 fragments for efficient production in Escherichia coli and enhanced antiproliferative activity", Protein Engineering, vol. 8, No. 10, pp. 1057-1062, (1995).
Becherer, et al., "Segment spanning residues 727-768 of the complement C3 sequence contains a neoantigenic site and accommodates the binding of CR1, Factor H, and Factor B", Biochemistry, 31, 1787-1794, (1992).
Dilillo, et al., "Selective and efficient inhibition of the alternative pathway of complement by a mAb that recognizes C3b/1C3b", Molecular Immunology, 43:1010-1019, (2006).
Hack, et al., "Disruption of the internal thioester bond in the third component of complement (C3) results in the exposure of neodeterminants also present on activation products of C3", The journal of immunology, vol. 141, pp. 1602-1609, (1988).
Ham et al., "Media and growth requirements" Methods in Enzymology, 1979; vol. 58, pp. 44-93.
Oglesby et al., "Protection of mammalian cells from complement-mediated lysis . . . ", TransAssoc Am Physicians, 1991; 104: 164-72.
Pluckthun et al., "Antibodies from *Escherichia coli*", Handbook of Experimental Pharmacology, 1994; vol. 113, pp. 269-315.
Ross et al., "Membrane complement receptors specific for bound fragments of C3", Advances in Immunology, 1985; vol. 37, pp. 217-267.
Ham et al., "Media and growth requirements", Methods in Enzymology 58: 44-93 (1979).
Oglesby et al., "Protection of mammalian cells from complement-mediated lysis", Trans. Assoc. Am. Physicians 104: 164-172 (1991).
Pluckthun et al., "Antibodies from *Escherichia coli*," Handbook of Experimental Pharmacology 133: 269-315 (1994).
Ross et al., "Membrane complement receptors specific for bound fragments of C3", Advances in Immunology 37: 217-267 (1985).

* cited by examiner

C3b Panning Results

| Project | Library | Enrichment | Clones Screened | Unique Clones |
|---|---|---|---|---|
| YW136 | VH | x 10,000 | 300 (P4&P3) | ~ 37 |
| YW144 | VH/VL | x 37,000 | 300 (P4&P3) | ~120 |

***Blocking with C3 after 1st round

FIG. 1

C3b Phage Competition Results

| Clone | Relative Phage IC$_{50}$ | |
|---|---|---|
| YW136.1.55 | ~50nM | * |
| YW136.1.6 | ~50nM | * |
| YW136.1.54 | ~100nM | |
| YW144.1.15 | ~100nM | |
| YW144.1.60 | ~50nM | * |
| YW144.2.43 | ~50nM | * |
| YW144.2.45 | ~50nM | * |
| YW144.2.91 | ~100nM | |
| YW144.P3.10 | ~100nM | |
| YW144.P3.24 | ~10nM | ** |
| YW144.P3.39 | ~100nM | |
| YW144.P3.49 | ~50nM | * |
| YW144.P3.65 | ~100nM | |

FIG. 2

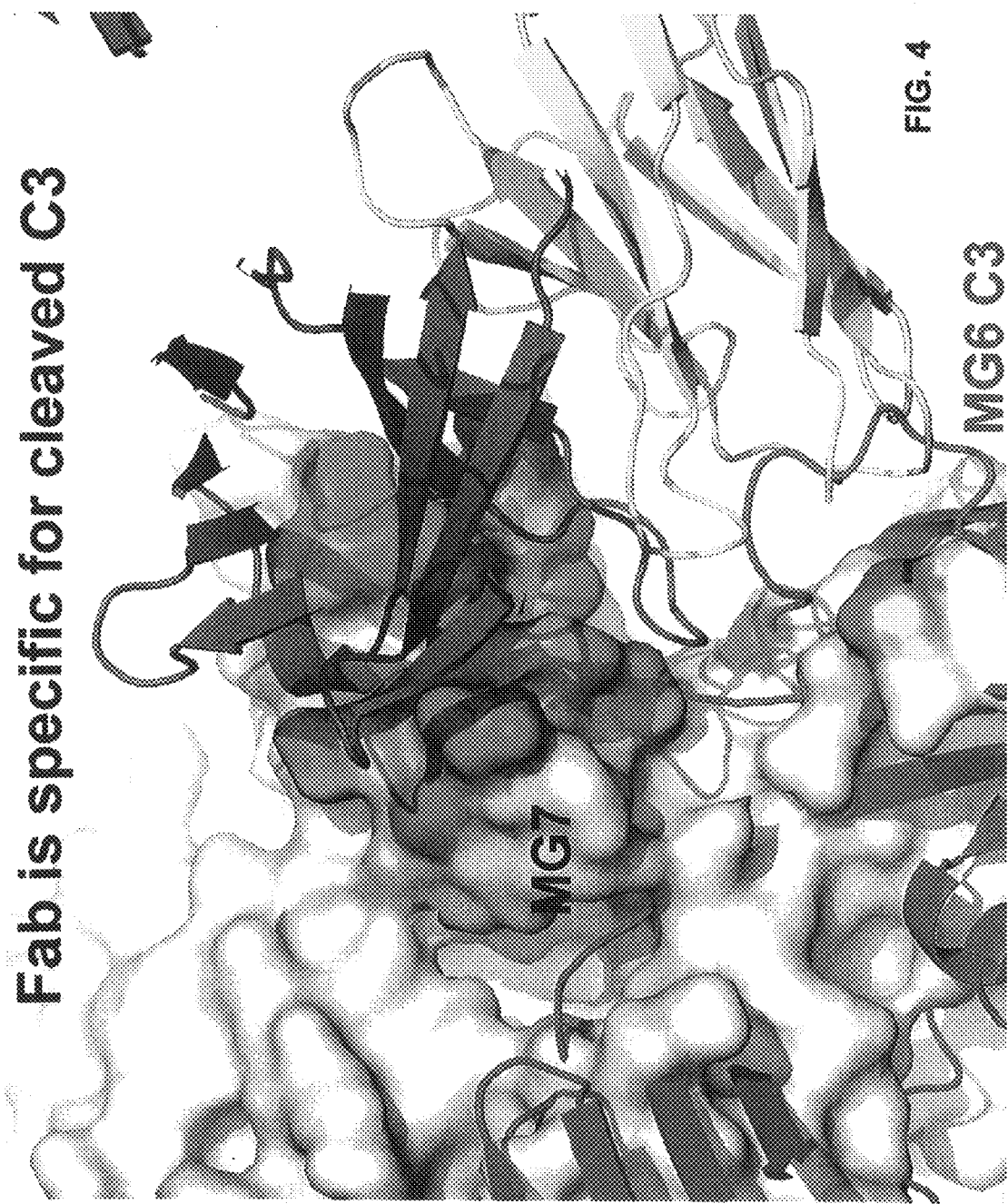

Sequence of heavy- and light chain of Fab S77 and residues on S77 in contact with C3b

S77 HC
MGWSCIILFLVATATGAYAEVQLVESGGGLVQPGGSLRLSCAAS
<CDR H1>GFSFTSSSVSWVRQAPGKGLEWVGL<CDR
H2>IYPYNGFNYYADSVKGRFTISADTSKNTAYLQMNSLRAEDTAVYYC
AR<CDR H3>NALYGSGGYYAMDYWGQGTLVTVSSA
<End reformatted sequence>

S77 LC
MGWSCIILFLVATATGVHSDIQMTQSPSSLSASVGDRVTITC<CDR
L1>RASQDVSTAVAWYQQKPGKAPKLLIY<CDR
L2>SASFLYSGVPSRFSGSGSGTDFTLTISSLQPEDFATYYC<CDR
L3>QQSYATLPTFEQGTKVEIK
<End reformatted sequence>

FIG. 5

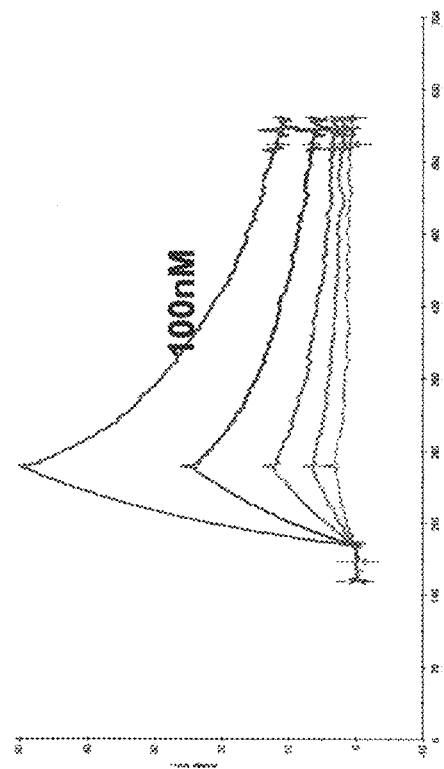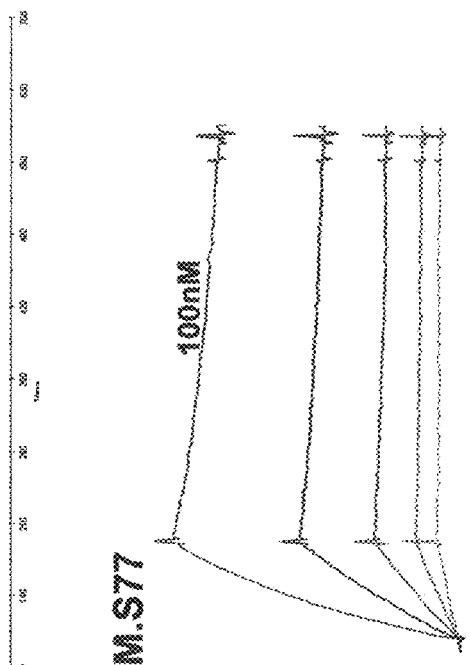
FIG. 6

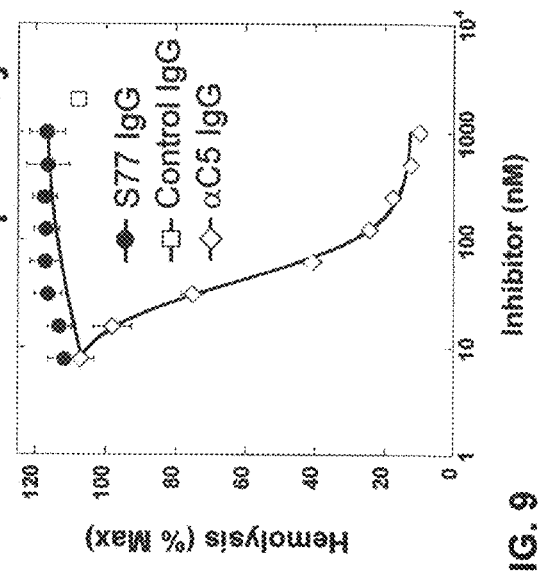
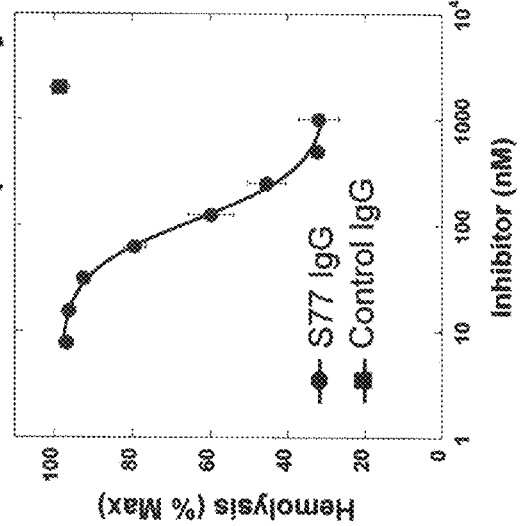
FIG. 9

LIGHT CHAIN

```
1   DIQMTQSPSSLSASVGDRVTITCRASQDVNTAVAWYQQKPGKAPK    45
46  LLIYSASFLYSGVPSRFSGSRSGTDFTLTISSLQPEDFATYYCQQ    90
91  HYTTPPTFGQGTKVEIKRTVAAPSVFIFPPSDEQLKSGTASVVCL    135
136 LNNFYPREAKVQWKVDNALQSGNSQESVTEQDSKDSTYSLSSTLT    180
181 LSKADYEKHKVYACEVTHQGLSSPVTKSFNRGEC    214
```

FIG. 18A

HEAVY CHAIN

```
  1 EVQLVESGGGLVQPGGSLRLSCAASGFNIKDTYIHWVRQAPGKGL   45
 46 EWVARIYPTNGYTRYADSVKGRFTISADTSKNTAYLQMNSLRAED   90
 91 TAVYYCSRWGGDGFYAMDYWGQGTLVTVSSASTKGPSVFPLAPSS  135
136 KSTSGGTAALGCLVKDYFPEPVTVSWNSGALTSGVHTFPAVLQSS  180
181 GLYSLSSVVTVPSSSLGTQTYICNVNHKPSNTKVDKKVEPKSCDK  225
226 THTCPPCPAPELLGGPSVFLFPPKPKDTLMISRTPEVTCVVVDVS  270
271 HEDPEVKFNWYVDGVEVHNAKTKPREEQYNSTYRVVSVLTVLHQD  315
316 WLNGKEYKCKVSNKALPAPIEKTISKAKGQPREPQVYTLPPSREE  360
361 MTKNQVSLTCLVKGFYPSDIAVEWESNGQPENNYKTTPPVLDSDG  405
406 SFFLYSKLTVDKSRWQQGNVFSCSVMHEALHNHYTQKSLSLSPG   449
```

FIG. 18B

Residues on C3b in contact with S77

>From C3b:
SER A 548 28.00 34.57 % of 81.00
ASP A 550 10.00 7.69 % of 130.00
ARG A 551 81.00 60.90 % of 133.00
VAL A 554 20.00 34.48 % of 58.00
ASP A 732 54.00 54.00 % of 100.00
MET A 804 1.00 5.88 % of 17.00
GLN A 805 11.00 30.56 % of 36.00
ASP A 806 48.00 62.34 % of 77.00
ARG A 833 66.00 72.53 % of 91.00
GLN A 834 3.00 2.88 % of 104.00
ASN A 835 121.00 86.43 % of 140.00
GLN A 836 56.00 98.25 % of 57.00
GLU A 837 80.00 70.18 % of 114.00
LEU A 838 4.00 80.00 % of 5.00
LYS A 839 25.00 28.41 % of 88.00
PRO A 867 8.00 22.22 % of 36.00
PRO A 868 26.00 60.47 % of 43.00
TYR A 895 1.00 4.35 % of 23.00
HIS A 896 101.00 87.83 % of 115.00
HIS A 897 67.00 91.78 % of 73.00
PHE A 898 166.00 80.98 % of 205.00
ILE A 899 49.00 70.00 % of 70.00 CHAIN A DIFF-AREA: 1026.0 ( 1.47 % of 69629.0 total AREA for this chain)

Fig. 19

Fab S77 residues in contact with C3b

S77 LC in contact with C3b:
ASP B 28 41.00 44.09 % of 93.00
SER B 30 15.00 37.50 % of 40.00
LEU B 46 3.00 33.33 % of 9.00
TYR B 49 36.00 55.38 % of 65.00
TYR B 55 15.00 30.00 % of 50.00
TYR B 92 38.00 40.43 % of 94.00

Residues on S77 HC in contact with C3b:
VAL B1002 13.00 56.52 % of 23.00
GLY B1026 8.00 13.33 % of 60.00
PHE B1027 17.00 58.62 % of 29.00
SER B1028 34.00 49.28 % of 69.00
THR B1030 31.00 48.44 % of 64.00
SER B1031 96.00 100.00 % of 96.00
SER B1032 18.00 100.00 % of 18.00
SER B1033 3.00 60.00 % of 5.00
TYR B1052 65.00 86.67 % of 75.00
TYR B1054 76.00 43.93 % of 173.00
ASN B1055 22.00 20.75 % of 106.00
PHE B1057 16.00 16.67 % of 96.00
ARG B1098 41.00 100.00 % of 41.00
ASN B1099 8.00 72.73 % of 11.00
ALA B1100 30.00 100.00 % of 30.00
LEU B1101 98.00 90.74 % of 108.00
TYR B1102 37.00 75.51 % of 49.00
GLY B1103 10.00 24.39 % of 41.00
SER B1104 65.00 67.71 % of 96.00
GLY B1105 27.00 29.03 % of 93.00
GLY B1106 17.00 68.00 % of 25.00
TYR B1107 2.00 5.88 % of 34.00
ALA B1109 4.00 100.00 % of 4.00
ASP B1111 12.00 46.15 % of 26.00
TYR B1112 11.00 14.29 % of 77.00

Fig. 20 ptideC3B ANTIBODIES AND METHODS FOR THE PREVENTION AND TREATMENT OF COMPLEMENT-ASSOCIATED DISORDERS

CROSS-REFERENCE TO RELATED APPLICATIONS

This application is a divisional of U.S. application Ser. No. 12/157,073, filed Jun. 6, 2008, now issued as U.S. Pat. No. 8,012,473, which is a non-provisional application filed under 37 CFR 1.53(b)(1), claiming priority under 35 USC §119(e) to U.S. Provisional application Nos. 61/055,068 filed May 21, 2008, and 60/933,721, filed Jun. 7, 2007, the contents of which are incorporated herein by reference.

FIELD OF THE INVENTION

The present invention concerns antibodies to C3b and the prevention and treatment of complement-associated disorder using such antibodies.

BACKGROUND OF THE INVENTION

The complement system is a complex enzyme cascade made up of a series of serum glycoproteins, that normally exist in inactive, pro-enzyme form. Two main pathways, the classical and the alternative pathway, can activate complement, which merge at the level of C3, where two similar C3 convertases cleave C3 into C3a and C3b.

Macrophages are specialist cells that have developed an innate capacity to recognize subtle differences in the structure of cell-surface expressed identification tags, so called molecular patterns (Taylor, et al., *Eur J Immunol* 33, 2090-2097 (2003); Taylor, et al. *Annu Rev Immunol* 23, 901-944 (2005)). While the direct recognition of these surface structures is a fundamental aspect of innate immunity, opsonization allows generic macrophage receptors to mediate engulfment, increasing the efficiency and diversifying recognition repertoire of the phagocyte (Stuart and Ezekowitz, *Immunity* 22, 539-550 (2005)). The process of phagocytosis involves multiple ligand-receptor interactions, and it is now clear that various opsonins, including immunoglobulins, collectins, and complement components, guide the cellular activities required for pathogen internalization through interaction with macrophage cell surface receptors (reviewed by Aderem and Underhill, *Annu Rev Immunol* 17, 593-623 (1999); Underhill and Ozinsky, *Annu Rev Immunol* 20, 825-852 (2002)). While natural immunoglobulins encoded by germline genes can recognize a wide variety of pathogens, the majority of opsonizing IgG is generated through adaptive immunity, and therefore efficient clearance through Fc receptors is not immediate (Carroll, *Nat Immunol* 5, 981-986 (2004)). Complement, on the other hand, rapidly recognizes pathogen surface molecules and primes the particle for uptake by complement receptors (Brown, *Infect Agents Dis* 1, 63-70 (1991)).

Complement consists of over 30 serum proteins that opsonize a wide variety of pathogens for recognition by complement receptors. Depending on the initial trigger of the cascade, three pathways can be distinguished (reviewed by (Walport, *N Engl J Med* 344, 1058-1066 (2001)). All three share the common step of activating the central component C3, but they differ according to the nature of recognition and the initial biochemical steps leading to C3 activation. The classical pathway is activated by antibodies bound to the pathogen surface, which in turn bind the C1q complement component, setting off a serine protease cascade that ultimately cleaves C3 to its active form, C3b. The lectin pathway is activated after recognition of carbohydrate motifs by lectin proteins. To date, three members of this pathway have been identified: the mannose-binding lectins (MBL), the SIGN-R1 family of lectins and the ficolins (Pyz et al., *Ann Med* 38, 242-251 (2006)) Both MBL and ficolins are associated with serine proteases, which act like C1 in the classical pathway, activating components C2 and C4 leading to the central C3 step. The alternative pathway contrasts with both the classical and lectin pathways in that it is activated due to direct reaction of the internal C3 ester with recognition motifs on the pathogen surface. Initial C3 binding to an activating surface leads to rapid amplification of C3b deposition through the action of the alternative pathway proteases Factor B and Factor D. Importantly, C3b deposited by either the classical or the lectin pathway also can lead to amplification of C3b deposition through the actions of Factors B and D. In all three pathways of complement activation, the pivotal step in opsonization is conversion of the component C3 to C3b. Cleavage of C3 by enzymes of the complement cascades exposes the thioester to nucleophilic attack, allowing covalent attachment of C3b onto antigen surfaces via the thioester domain. This is the initial step in complement opsonization. Subsequent proteolysis of the bound C3b produces iC3b, C3c and C3dg, fragments that are recognized by different receptors (Ross and Medof, *Adv Immunol* 37, 217-267 (1985)). This cleavage abolishes the ability of C3b to further amplify C3b deposition and activate the late components of the complement cascade, including the membrane attack complex, capable of direct membrane damage. However, macrophage phagocytic receptors recognize C3b and its fragments preferentially; due to the versatility of the ester-bond formation, C3-mediated opsonization is central to pathogen recognition (Holers et al., *Immunol Today* 13, 231-236 (1992)), and receptors for the various C3 degradation products therefore play an important role in the host immune response.

C3 itself is a complex and flexible protein consisting of 13 distinct domains. The core of the molecule is made up of 8 so-called macroglobulin (MG) domains, which constitute the tightly packed α and β chains of C3. Inserted into this structure are CUB (Clr/Cls, Uegf and Bone mophogenetic protein-1) and TED domains, the latter containing the thioester bond that allows covalent association of C3b with pathogen surfaces. The remaining domains contain C3a or act as linkers and spacers of the core domains. Comparison of C3b and C3c structures to C3 demonstrate that the molecule undergoes major conformational rearrangements with each proteolysis, which exposes not only the TED, but additional new surfaces of the molecule that can interact with cellular receptors (Janssen and Gros, *Mol Immunol* 44, 3-10 (2007)).

In order to prevent unwanted complement activation, most mammalian cells are equipped with regulators that block complement amplification on host self cells (Hourcade et al. *Adv Immunol* 45:381 (1989)). In the absence of these intrinsic regulators, serum exposure results in the generation of complement split product that in turn facilitate inflammation and tissue damage (Oglesby et al. *J Exp Med* 175:1547 (1992) and Oglesby et al., *Trans Assoc. Am. Physicians* 104:164 (1991)). Non-cellular surfaces that lack intrinsic complement regulators are therefore especially prone to complement attack and are fully dependent on protection by soluble complement regulators in serum. Uncontrolled complement activation due to the lack of appropriate complement regulation has been associated with various chronic inflammatory diseases and degenerative diseases. Dominant in this inflammatory cascade are the complement split products C3a and C5a that function as chemo-attractant and activators of neutrophils and inflammatory macrophages via the C3a and C5a receptors (Mollnes et al., *Trends Immunol* 23:61 (2002)). Properdin, released from neutrophils, further amplifies the inflammatory cascade through stabilization of the AP convertase (Lutz and Jelezarova, *Mol. Immunol.* 43:2 (2006)). Complement activation has been shown to be an important component driving inflammation in immune-complex mediated diseases such as membranoproliferative glomerulonephritis, nephrotoxic nephritis and arthritis (Walport, *N. Engl. J. Med.* 344:1058 (2001); Thurman and Holers, *J. Immunol.* 176:1305 (2006); Banda et al., *J. Immunol.* 171:2109 (2003); Weisman et al., *Science* 249:146 (1990); Morgan and Harris, *Mol. Immunol.* 40:159 (2003)), as well as age-related macular degeneration (Anderson et al., *Am. J. Ophthalmol.* 134:411 (2002); Donoso et al., *Surv. Ophthalmol.* 51:137 (2006); Gold et al., *Natl. Genet.* 38:458 (2006); Hageman et al., *Proc. Natl. Acad. Sci. USA* 102:7227 (2005); Hageman et al., *Ann. Med.* 38:592 (2006); Hageman et al., *Prog. Retin. Eye Res.* 20:705 (2001)).

Most regulators of complement activation act at the level of C3b, the central component of the complement convertases. These natural regulators of complement activation are typically large in size (>100 kDa) and difficult to develop as a therapeutic reagent. Accordingly, there is a need for therapeutic agents to prevent and treat complement-associated disorders by blocking C3b.

SUMMARY OF THE INVENTION

The present invention concerns the development of antibodies that specifically recognize breakdown fragments of C3, and not native C3, thus avoiding the native C3 acting as a "sink" for the antibodies. More particularly, the invention concerns C3b specific antibodies and antibody fragments and their use in the treatment of complement-associated diseases.

In one aspect, the invention concerns a method for the prevention or treatment of a complement-associated disorder comprising administering to a subject in need an effective amount of a C3b antagonist that is a selective inhibitor of the alternative complement pathway.

In one embodiment, the subject is a mammal. In another embodiment, the subject is a human.

In a further embodiment, the C3b antagonist is an antibody recognizing an epitope on an active degradation product of C3 but not on C3.

In a still further embodiment, the C3b antagonist is an antibody or an antibody fragment selectively binding to C3b.

In a different embodiment, the antibody inhibits the binding of C5 to C3b.

In another embodiment, the antibody binds to an epitope including residues of the C3b epitope recognized by antibody S77.

In yet another embodiment, the antibody binds essentially to the same epitope as antibody S77.

In a further embodiment, the antibody competitively inhibits the binding of antibody S77.

In a still further embodiment, the antibody binds to a C3b epitope comprising residues that are in contact with antibody S77.

In an additional embodiment, the antibody comprises an antigen binding site comprising antibody S77 residues that are in contact with C3b.

In a preferred embodiment, the antibody comprises the heavy (SEQ ID NOS 2-4) and/or light (SEQ ID NOS 6-8) chain CDR sequences of antibody S77 and/or is the S77 antibody or a fragment thereof.

In various embodiments, the antibody can be human, humanized or chimeric.

In other embodiments, the antibody fragment is selected from the group consisting of Fab, Fab', F(ab')$_2$, scFv, (scFv)$_2$, dAb, complementarity determining region (CDR) fragments, linear antibodies, single-chain antibody molecules, minibodies, diabodies, and multispecific antibodies formed from antibody fragments.

The methods of the present invention include prevention or treatment of any complement-associated disorder, including inflammatory and autoimmune diseases, such as, for example, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

In a particular embodiment, the complement-associated disorder is a complement-associated eye condition, such as age-related macular degeneration (AMD) or choroidal neovascularization (CNV).

In another aspect, the invention concerns an anti-C3b antibody selectively binding to C3b and not to C3 and inhibiting the binding of C5 to C3b.

In one embodiment, the antibody binds to an epitope including residues of the C3b epitope recognized by antibody S77.

In another embodiment, the antibody binds essentially to the same epitope as antibody S77.

In yet another embodiment, the antibody competitively inhibits the binding of antibody S77.

In a different embodiment, the antibody binds to a C3b epitope comprising residues that are in contact with antibody S77.

In a further embodiment, the antibody comprises an antigen binding site comprising antibody S77 residues that are in contact with C3b.

In a still further embodiment, the antibody comprises the heavy (SEQ ID NOS 2-4) and/or light (SEQ ID NOS 6-8) chain CDR sequences of antibody S77 or is antibody S77 or a fragment thereof.

In various embodiments, the antibody a human, humanized or chimeric antibody.

The antibody fragment can, for example, be selected from the group consisting of Fab, Fab', F(ab')$_2$, scFv, (scFv)$_2$, dAb, complementarity determining region (CDR) fragments, linear antibodies, single-chain antibody molecules, minibodies, diabodies, and multispecific antibodies formed from antibody fragments.

In another aspect, the invention concerns a pharmaceutical composition comprising a C3b antagonist, such as a C3b antibody of the in admixture with a pharmaceutically acceptable carrier.

In a particular embodiment, the pharmaceutical composition is for use in the treatment of a complement-associated disorder.

In a further aspect, the invention concerns a kit comprising a container comprising a C3b antagonists or C3b antibody of the present invention, or a pharmaceutical composition comprising such antagonist or antibody, and instructions for administration of the antibody or pharmaceutical composition for the treatment of a complement-associated disorder.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIG. 1. C3b panning results in an antibody phage library.

FIG. 2. Phage competition results with various C3b antibody clones

FIG. 4. Close-up of binding interaction of antibody S77 with C3b. C3b is shown in a surface representation, a ribbon diagram in cyan represents C3 superimposed on the C3b structure. The HC and LC of S77 are indicated as a ribbon diagram in dark green and yellow. The surface of C3b is colored according to the distance to S77. All atoms closer than 4.7 Å, 4.0 Å and 3.5 Å are colored yellow, orange and red respectively. Note that the LC of S77 is clashing with C3. However loop of C3 might be able to move.

FIG. 5. Amino-acid sequences of the heavy (SEQ ID NOS 2-4) and light (SEQ ID NOS 6-8) chains of antibody S77 Fab fragment. Indicated in red are the residues that are in close contact with C3b.

FIG. 6. Binding affinity of the parent antibody YW 144.2.43 Fab and its affinity matured version: 144.2.43.S77 Fab (S77 Fab).

FIG. 9. IgG antibody S77 selectively inhibits the alternative- but not classical-pathway of complement. Rabbit erythrocytes and sheep erythrocytes were incubated in C1q- and factor B-depleted serum and hemolysis monitored in the presence of increasing concentration of inhibitor or control protein. Hemolysis was expressed as the percentage of maximal hemolysis in the absence of inhibitor.

FIGS. 18A and 18B. Amino acid sequences of anti-HER2 antibody rhuMAB 4D5-8 light (SEQ ID NO: 13) and heavy (SEQ ID NO: 14) chain variable regions.

FIG. 19. Residues on C3b in contact with the HC and LC of S77 Fab (Residues 833-839 encompass SEQ ID NO: 15; Residues 895-899 encompass SEQ ID NO: 16).

FIG. 20. Residues on S77 Fab in contact with C3b (Residues 1030-1033 encompass SEQ ID NO: 17; Residues 1098-1107 encompass SEQ ID NO: 18).

DETAILED DESCRIPTION OF THE PREFERRED EMBODIMENT

I. Definitions

The terms "C3" and "complement C3" are used interchangeably, and refer to native sequence C3 polypeptides.

Figure 21:
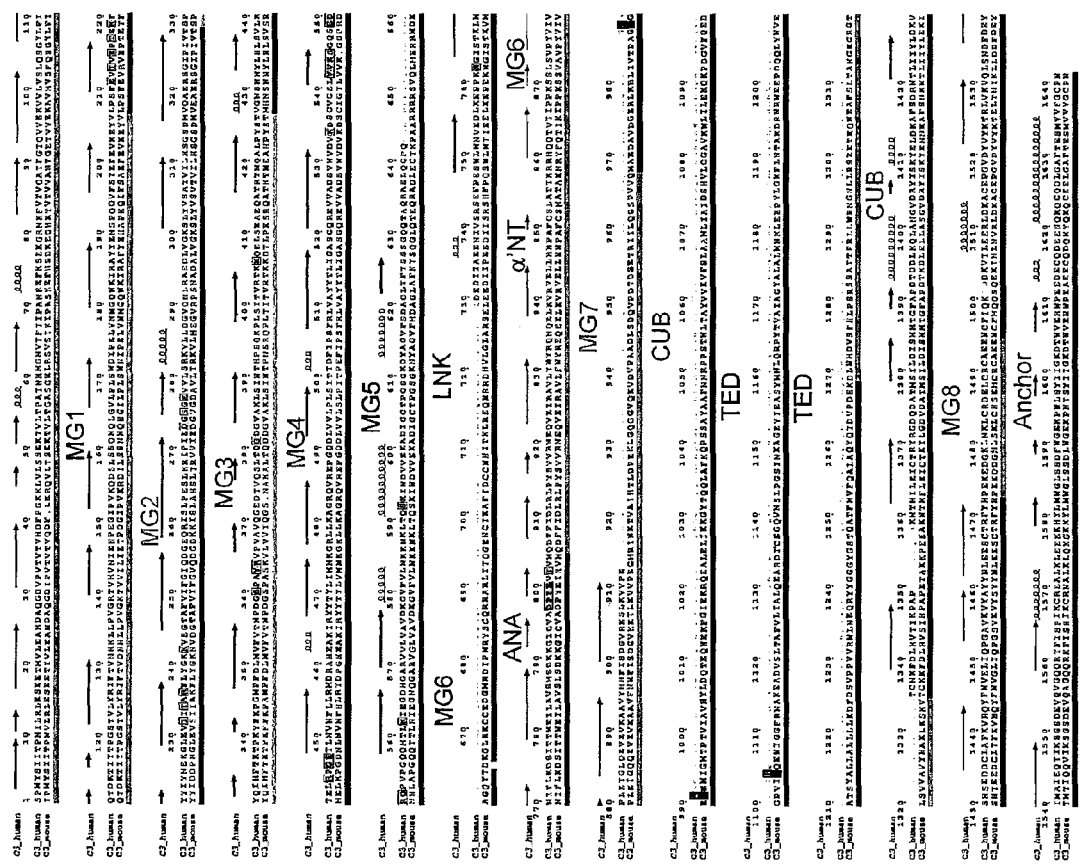
FIG. 21. Amino acid sequences of human complement factor C3 (SEQ ID NO: 9) and mouse complement factor C3 (SEQ ID NO: 10).

A "native sequence C3", is a polypeptide having the same amino acid sequence as a C3 polypeptide derived from nature, regardless of its mode of preparation. Thus, native sequence C3 can be isolated from nature or can be produced by recombinant and/or synthetic means. The term "native sequence C3" specifically encompasses naturally-occurring variant forms (e.g., alternatively spliced forms) and naturally-occurring allelic variants of C3, as well as structural conformational variants having the same amino acid sequence as a C3 polypeptide derived from nature. Native sequence C3 polypeptides specifically include native sequence human C3 (FIG. 21, SEQ ID NO: 9; see, also De Bruijn and Fey, *Proc. Natl. Acad. Sci. USA* 82:708-712) and polypeptides of non-human animals, including higher primates and other non-human mammals, such as the mouse C3 sequence shown in FIG. 21, SEQ ID NO: 10).

The terms "C3b" is used herein to refer to a native sequence C3b polypeptide produced from C3b after cleavage by C3 convertase releasing the anaphylatoxin C3a fragment from the amino terminus of the C3 α-chain and leaving behind C3b. The term "native sequence" has the same meaning as that defined in connection with C3, and specifically includes the native sequence human C3b of SEQ ID NO: 9.

The term "C3b antagonist" is used in the broadest sense, and includes any molecule that is capable of neutralizing, blocking, partially or fully inhibiting, abrogating, reducing or interfering with a C3 biological activity. C3b antagonists include, without limitation, anti-C3b antibodies and antigen-binding fragments thereof, other binding polypeptides, peptides, and non-peptide small molecules, that bind to C3b and are capable of neutralizing, blocking, partially or fully inhibiting, abrogating, reducing or interfering with C3b activities, such as the ability of C3b to participate in the pathology of a complement-associated disorder. The C3b antagonists, such as C3b antibodies, herein specifically recognize C3b and not its precursor, C3.

A "small molecule" is defined herein to have a molecular weight below about 600, preferably below about 1000 daltons.

"Active" or "activity" or "biological activity" in the context of a C3b antagonist, such as a C3b antibody, of the present invention is the ability the antagonize (partially or fully inhibit) a biological activity of C3b. A preferred biological activity of a C3b antagonist is the ability to achieve a measurable improvement in the state, e.g. pathology, of a C3b-associated disease or condition, such as, for example, a complement-associated disorder. The activity can be determined in in vitro or in vivo tests, including binding assays, using a relevant animal model, or human clinical trials.

The term "complement-associated disorder" is used herein in the broadest sense and includes all diseases and pathological conditions the pathogenesis of which involves abnormalities of the activation of the complement system, such as, for example, complement deficiencies. The term specifically include diseases and pathological conditions that benefit from the inhibition of C3 convertase. The term additionally includes diseases and pathological conditions that benefit from inhibition, including selective inhibition, of the alternative complement pathway. Complement-associated disorders include, without limitation, inflammatory diseases and autoimmune diseases, such as, for example, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

The term "complement-associated eye condition" is used herein in the broadest sense and includes all eye conditions and diseases the pathology of which involves complement, including the classical and the alternative pathways, and in particular the alternative pathway of complement. Specifically included within this group are all eye conditions and diseases the associated with the alternative pathway, the occurrence, development, or progression of which can be controlled by the inhibition of the alternative pathway. Complement-associated eye conditions include, without limitation, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

The term "inflammatory disease" and "inflammatory disorder" are used interchangeably and mean a disease or disorder in which a component of the immune system of a mammal causes, mediates or otherwise contributes to an inflammatory response contributing to morbidity in the mammal. Also included are diseases in which reduction of the inflammatory response has an ameliorative effect on progression of the disease. Included within this term are immune-mediated inflammatory diseases, including autoimmune diseases.

The term "T-cell mediated" disease means a disease in which T cells directly or indirectly mediate or otherwise contribute to morbidity in a mammal. The T cell mediated disease may be associated with cell mediated effects, lymphokine mediated effects, etc. and even effects associated with B cells if the B cells are stimulated, for example, by the lymphokines secreted by T cells.

Examples of immune-related and inflammatory diseases, some of which are T cell mediated, include, without limitation, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection, graft-versus host disease, Alzheimer's disease, and atherosclerosis.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In treatment of an immune related disease, a therapeutic agent may directly alter the magnitude of response of a component of the immune response, or render the disease more susceptible to treatment by other therapeutic agents, e.g., antibiotics, antifungals, anti-inflammatory agents, chemotherapeutics, etc.

The "pathology" of a disease, such as a complement-associated disorder, includes all phenomena that compromise the well-being of the patient. This includes, without limitation, abnormal or uncontrollable cell growth (neutrophilic, eosinophilic, monocytic, lymphocytic cells), antibody production, auto-antibody production, complement production, interference with the normal functioning of neighboring cells, release of cytokines or other secretory products at abnormal levels, suppression or aggravation of any inflammatory or immunological response, infiltration of inflammatory cells (neutrophilic, eosinophilic, monocytic, lymphocytic) into cellular spaces, etc.

The term "mammal" as used herein refers to any animal classified as a mammal, including, without limitation, humans, higher primates, domestic and farm animals, and zoo, sports or pet animals such horses, pigs, cattle, dogs, cats and ferrets, etc. In a preferred embodiment of the invention, the mammal is a human.

Administration "in combination with" one or more further therapeutic agents includes simultaneous (concurrent) and consecutive administration in any order.

"Therapeutically effective amount" is the amount of a "C3b antagonist," such as a "C3b antibody" which is required to achieve a measurable improvement in the state, e.g. pathology, of the target disease or condition, such as, for example, a complement-associated disorder.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42 C; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/mL denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a polypeptide of the invention fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The term "antibody" is used in the broadest sense and specifically covers, without limitation, single antibodies recognizing a breakdown fragment of C3 but not native C3, such as anti-C3b monoclonal antibodies specifically binding to C3b, and antibody compositions with polyepitopic specificity. The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352:624-628 and Marks et al. (1991) *J. Mol. Biol.* 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) *Proc. Natl. Acad. Sci. USA* 81:6851-6855).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al. (1986) *Nature* 321:522-525; Riechmann et al. (1988) *Nature* 332:323-329; and Presta (1992) *Curr. Op. Struct. Biol.* 2:593-596.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e. has a binding affinity ($K_d$) value of no more than about $1 \times 10^{-7}$ M, preferably no more than about $1 \times 10^{-8}$ M and most preferably no more than about $1 \times 10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In a preferred embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) *J. Mol. Biol.* 196:901-917). In some instances, a complementarity determining region can include amino acids from both a CDR region defined according to Kabat and a hypervariable loop. For example, the CDRH1 of the heavy chain of antibody 4D5 includes amino acids 26 to 35.

"Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g. NNK, NNS, XYZ, DVK and the like. A "non-random codon set", as used herein, thus refers to a codon set that encodes select amino acids that fulfill partially, preferably completely, the criteria for amino acid selection as described herein. Synthesis of oligonucleotides with selected nucleotide "degeneracy" at certain positions is well known in that art, for example the TRIM approach (Knappek et al. (1999) *J. Mol. Biol.* 296:57-86); Garrard & Henner (1993) *Gene* 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

The term "antibody fragment" is used herein in the broadest sense and includes, without limitation, Fab, Fab', F(ab')$_2$, scFv, (scFv)$_2$, dAb, and complementarity determining region (CDR) fragments, linear antibodies, single-chain antibody molecules, minibodies, diabodies, and multispecific antibodies formed from antibody fragments.

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (1993) *Proc. Natl. Acad. Sci. USA* 90:6444-6448.

The expression "linear antibodies" refers to the antibodies described in Zapata et al. (1995 *Protein Eng*, 8(10):1057-1062). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman (1992) *Curr. Opin. Struct. Biol.* 3:355-362, and references cited therein. In a monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells (1991) *Methods: A companion to Methods in Enzymology* 3:205-0216.

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody, preferably using a computer program such as the InsightII program (Accelrys, San Diego, Calif.). Solvent accessible positions can also be determined using algorithms known in the art (e.g., Lee and Richards (1971) *J. Mol. Biol.* 55, 379 and Connolly (1983) *J. Appl. Cryst.* 16, 548). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios (1994) *Comput. Chem.* 18(4): 377-386.

II. Detailed Description

The Complement System

Complement plays a crucial role in the body's defense, and, together with other components of the immune system, protect the individual from pathogens invading the body. However, if not properly activated or controlled, complement can also cause injury to host tissues. Inappropriate activation of complement is involved in the pathogenesis of a variety of diseases, referred to as complement associated diseases or disorders, such as immune complex and autoimmune diseases, and various inflammatory conditions, including complement-mediated inflammatory tissue damage. The pathology of complement-associated disorders varies, and might involve complement activation for a long or short period of time, activation of the whole cascade, only one of the cascades (e.g. classical or alternative pathway), only some components of the cascade, etc. In some diseases complement biological activities of complement fragments result in tissue injury and disease. Accordingly, inhibitors of complement have high therapeutic potential. Selective inhibitors of the alternative pathway would be particularly useful, because clearance of pathogens and other organisms from the blood through the classical pathway will remain intact.

C3b Antibodies and their Use in the Prevention and Treatment of Complement-Associated Disorders The present invention is based, at least in part, on the development of antibodies that specifically recognize breakdown fragments of C3, and not native C3. In particular, the invention concerns antibodies recognizing and specifically binding to C3b, developed using human combinatorial antibody libraries and phage display, where enrichment for C3b specific phages was achieved by blocking with saturating amounts of C3. Using this methodology, we were able to develop antibodies that are specific for the activated forms of C3. In addition, these human antibodies were further affinity matured, thus increasing their potency in in vitro hemolytic assays. A Fab fragment was generated by cloning and shown to retain a high potency for inhibiting complement activation through the alternative pathway. A co-structure of the Fab (designated S77) in complex with C3b was solved and the residues involved in the C3b-S77 interaction were mapped. To our knowledge, this is the first phage-derived antibody with selectivity for C3 fragments that inhibits the alternative pathway of complement.

The antibodies and other C3b specific antagonists of the present invention are useful in the prevention and treatment of complement-associated disorders. Specific examples of complement-associated diseases include, without limitation, rheumatoid arthritis (RA), acute respiratory distress syndrome (ARDS), remote tissue injury after ischemia and reperfusion, complement activation during cardiopulmonary bypass surgery, dermatomyositis, pemphigus, lupus nephritis and resultant glomerulonephritis and vasculitis, cardiopulmonary bypass, cardioplegia-induced coronary endothelial dysfunction, type II membranoproliferative glomerulonephritis, IgA nephropathy, acute renal failure, cryoglobulemia, antiphospholipid syndrome, macular degenerative diseases and other complement-associated eye conditions, such as age-related macular degeneration (AMD), choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, retinal neovascularization, as well as allo-transplantation, hyperacute rejection, hemodialysis, chronic occlusive pulmonary distress syndrome (COPD), asthma, and aspiration pneumonia.

A more extensive list of inflammatory conditions as examples of complement-associated diseases includes, for example, inflammatory bowel disease (IBD), systemic lupus erythematosus, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vaculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic polyneuropathy, hepatobiliary diseases such as infectious hepatitis (hepatitis A, B, C, D, E and other nonhepatotropic viruses), autoimmune chronic active hepatitis, primary biliary cirrhosis, granulomatous hepatitis, and sclerosing cholangitis, inflammatory and fibrotic lung diseases (e.g., cystic fibrosis), gluten-sensitive enteropathy, Whipple's disease, autoimmune or immune-mediated skin diseases including bullous skin diseases, erythema multiforme and contact dermatitis, psoriasis, allergic diseases of the lung such as eosinophilic pneumonia, idiopathic pulmonary fibrosis and hypersensitivity pneumonitis, transplantation associated diseases including graft rejection and graft-versus host disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid is infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stages have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class 1 molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis includes diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including eosinophilic pneumonia, idiopathic pulmonary fibrosis and hypersensitivity pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils. Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

The C3b antagonists, such as C3b antibodies, of the present invention are also useful for the prevention and treatment of complement-associated eye conditions (all eye conditions and diseases the pathology of which involves complement, including the classical and the alternative pathways, and in particular the alternative pathway of complement), such as, for example, macular degenerative diseases, such as all stages of age-related macular degeneration (AMD), including dry and wet (non-exudative and exudative) forms, choroidal neovascularization (CNV), uveitis, diabetic and other ischemia-related retinopathies, endophthalmitis, and other intraocular neovascular diseases, such as diabetic macular edema, pathological myopia, von Hippel-Lindau disease, histoplasmosis of the eye, Central Retinal Vein Occlusion (CRVO), corneal neovascularization, and retinal neovascularization. A preferred group of complement-associated eye conditions includes age-related macular degeneration (AMD), including non-exudative (wet) and exudative (dry or atrophic) AMD, choroidal neovascularization (CNV), diabetic retinopathy (DR), and endophthalmitis.

AMD is age-related degeneration of the macula, which is the leading cause of irreversible visual dysfunction in individuals over the age of 60. Two types of AMD exist, non-exudative (dry) and exudative (wet) AMD. The dry, or non-exudative, form involves atrophic and hypertrophic changes in the retinal pigment epithelium (RPE) underlying the central retina (macula) as well as deposits (drusen) on the RPE. Patients with nonexudative AMD can progress to the wet, or exudative, form of AMD, in which abnormal blood vessels called choroidal neovascular membranes (CNVMs) develop under the retina, leak fluid and blood, and ultimately cause a blinding disciform scar in and under the retina. Nonexudative AMD, which is usually a precursor of exudative AMD, is more common The presentation of nonexudative AMD varies; hard drusen, soft drusen, RPE geographic atrophy, and pigment clumping can be present. Complement components are deposited on the RPE early in AMD and are major constituents of drusen.

The present invention specifically concerns the treatment of high risk AMD, including category 3 and category 4 AMD. Category 3 AMD is characterized by the absence of advanced AMD in both eyes, at least one eye having a visual acuity of 20/32 or better with at least one large druse (e.g. 125 µm), extensive (as measured by drusen area) intermediate drusen, or geographic atrophy (GA) that does not involve the center of the macula, or any combination of these. Category 3 AMD (which is still considered "dry" AMD) has a high risk of conversion to choroidal neovascularization (CNV).

Category 4 high risk AMD (classified as "wet" AMD) is characterized by a visual acuity of 20/32 or better and no advanced AMD (GA involving the center of the macula or features of choroidal neovascularization) in index eye. The fellow eye is characterized by advanced AMD, or visual acuity less than 20/32 attributable to AMD maculopathy. Typically, high risk AMD, if untreated, rapidly progresses into choroidal neovascularization (CNV), at a rate about 10-30-times higher than the rate of progression for category 1 or 2 (not high risk) AMD.

C3b antagonists also find utility in the prevention of the progression of AMD (in particular, category 3 or category 4 AMD) into CNV, and/or the prevention of the development/progression of AMD or CNV in the non- or less effected fellow eye. In this context, the term "prevention" is used in the broadest sense to include, complete or partial blocking and slowing down of the progression of the disease as well as the delay of the unset of the more serious form of the disease. Patients who are at high risk of developing or progressing into high risk (category 4) AMD or CMV especially benefit from this aspect of the invention.

It is known that complement factor H(CFH) polymorphism is associated with the risk of an individual to develop AMD and/or CNV. Muations in CFH can activate complement, which in turn may lead to AMD/CNV. It has been recently reported that complement factor H(CFH) polymorphism accounts for 50% of the attributable risk of AMD (Klein et al., Science 308:385-9 (2005)). A common haplotype in CFH (HF1/CFH) has been found to predispose individuals to age-related macular degeneration (Hageman et al., Proc. Natl. Acad. Sci. USA, 102(2):7227-7232 (2005)). AMD has been segregated as an autosomal-dominant trait, with the disease locus mapping to chromosome 1q25-q31 between markers D15466 and D15413, with a maximum lod score of about 3.20 (Klein et al., Arch Opthalmol. 116(8):1082-9 (1998); Majewski et al., Am. J. Hum. Genet. 73(3):540-50 (2003); Seddon et al., Am. J. Hum. Genet. 73(4):780-90 (2003); Weeks et al., Am. J. Ophthalmol. 132(5):682-92 (2001); Iyengar et al., Am. J. Hum. Genet. 74(1):20-39 (2004)); chromosome 2q3/2q32 between markers D12S1391 and D2S1384, with a maximum lode score of 2.32/2.03 (Seddon et al., supra); 3p13, between markers D12S1300 and D12S1763, with a maximum lode score of 2.19 (Majewski et al., supra; Schick et al., Am. J. Hum. Genet. 72(6):1412-24 (2003)); 6q14 between markers D6S1056 and DS249 with a maximum lode score of 3.59/3.17 (Kniazeva et al., Am. J. Ophthlmol. 130(2):197-202 (2000)); 9q33, at marker D9S934, with a maximum lode score of 2.06 (Mejwski et al., supra); 10q26 at the marker D10S1230, with a maximum lode score of 3.06 (Majewski et al., supra; Iyengar et al., supra; Kenealy et al., Mol. Vis. 10:57-61 (2004); 17q25 at marker D17S928, maximum lode score of 3.16 (Weeks et al., supra); and 22q12 at marker D22S1045, maximum lode score of 2.0 (Seddon et al., supra). Accordingly, genetic screening is an important part of identifying patients who are particularly good candidates for preventative treatment, including prevention of the progression of the disease into a more severe form, such as from AMD to CNV.

Preparation and Selection of C3b Antibodies

The invention herein includes the production and use of antibodies that recognize C3b not its inactive precursor C3. Exemplary methods for generating antibodies are described in more detail in the following sections.

Anti-C3b antibodies are selected using a C3b polypeptide derived from a mammalian species. Preferably the polypeptide is human C3b. However, C3b polypeptides from other species such as murine C3b can also be used as the target antigen. The C3b antigens from various mammalian species may be isolated from natural sources. In other embodiments, the antigen is produced recombinantly or made using other synthetic methods known in the art.

The antibody selected will normally have a sufficiently strong binding affinity for the C3b antigen. For example, the antibody may bind human C3b with a $K_d$ value of no more than about 5 nM, preferably no more than about 2 nM, and more preferably no more than about 500 pM. Antibody affinities may be determined by a surface plasmon resonance based assay (such as the BIAcore assay as described in Examples); enzyme-linked immunoabsorbent assay (ELISA); and competition assays (e.g. RIA's), for example.

Also, the antibody may be subject to other biological activity assays, e.g., in order to evaluate its effectiveness as a therapeutic. Such assays are known in the art and depend on the target antigen and intended use for the antibody. Examples include the HUVEC inhibition assay (as described in the Examples below) and in vitro and in vivo assays described below for identifying antibodies that selectively block the alternative pathway and show activity in the prevention and/or treatment of at least one complement-associated disorder.

To screen for antibodies which bind to a particular epitope on the antigen of interest, a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest.

In a preferred embodiment, the anti-C3b antibodies of the present invention are selected using a unique phage display approach. The approach involves generation of synthetic human antibody phage libraries based on single framework template, design of sufficient diversities within variable domains, display of polypeptides having the diversified variable domains, and selection of candidate antibodies with high affinity to target C3b antigen. Enrichment for C3b specific phages, encode antibodies selectively blocking C3b but not C3, can be achieved, for example, by blocking with saturating amounts of C3, as described in the Example below.

Details of the phage display methods can be found, for example, in WO03/102157 published Dec. 11, 2003.

In one aspect, the antibody libraries can be generated by mutating the solvent accessible and/or highly diverse positions in at least one CDR of an antibody variable domain. Some or all of the CDRs can be mutated using the methods provided herein. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

Preferably, a library is created by substitution of original amino acids with variant amino acids in the CDRH3 region of the variable region of the heavy chain sequence. The resulting library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence $(DVK)_7$. In some embodiments, a library is created by substitution of residues 95-100a with amino acids encoded by both DVK and NNK codon sets. An example of an oligonucleotide set that is useful for creating these substitutions comprises the sequence $(DVK)_6(NNK)$. In another embodiment, a library is created by substitution of at least residues 95-100a with amino acids encoded by both DVK and NNK codon sets. An example of an oligonucleotide set that is useful for creating these substitutions comprises the sequence $(DVK)_5(NNK)$. Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK and NVK codon sets, as well as more limited diversity at N and/or C-terminal.

Diversity can also be generated in CDRH1 and CDRH2. The designs of CDR-H1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution sorting methods as described previously and herein below. Multiple sorting strategies may be employed. For example, one variation involves sorting on target bound to a solid, followed by sorting for a tag that may be present on the fusion polypeptide (e.g. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target C3b antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (e.g. utilizing DVK or NVT) provides for isolation of binders that may bind to different epitopes of a target antigen.

In another embodiment, a library or libraries with diversity in CDRH1, CDRH2 and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target C3b antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1 and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32 and 33. A CDRH2 library may be created with the sequence of humanized antibody 4D5 with variant amino acids at positions 50, 52, 53, 54, 56 and 58 using the predetermined codon sets.

The anti-C3b antibody generated from phage libraries can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay. For example, an anti-C3b antibody mutant preferably has a binding affinity for C3b which is at least about 10 fold stronger, preferably at least about 20 fold stronger, more preferably at least about 50 fold stronger, and sometimes at least about 100 fold or 200 fold stronger, than the binding affinity of the parent anti-C3b antibodies, such as, antibody S77.

To generate the antibody mutant, one or more amino acid alterations (e.g. substitutions) are introduced in one or more of the hypervariable regions of the parent antibody. Alternatively, or in addition, one or more alterations (e.g. substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) *Science* 233:747-753); interact with/effect the conformation of a CDR (Chothia et al. (1987) *J. Mol. Biol.* 196:901-917); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) *Science* 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined The ala-mutants produced this way are screened for their biological activity as described herein.

Normally one would start with a conservative substitution such as those shown below under the heading of "preferred substitutions". If such substitutions result in a change in biological activity (e.g. binding affinity), then more substantial changes, denominated "exemplary substitutions" in the following table, or as further described below in reference to amino acid classes, are introduced and the products screened. Preferred substitutions are listed in the table below.

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

hydrophobic: norleucine, met, ala, val, leu, ile;
neutral hydrophilic: cys, ser, thr, asn, gln;
acidic: asp, glu;
basic: his, lys, arg;
residues that influence chain orientation: gly, pro; and
aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis, PCR mutagenesis, and cassette mutagenesis of an earlier prepared mutant or a non-mutant version of the parent antibody. The preferred method for making mutants is site directed mutagenesis (see, e.g., Kunkel (1985) *Proc. Natl. Acad. Sci. USA* 82:488).

In certain embodiments, the antibody mutant will only have a single hypervariable region residue substituted. In other embodiments, two or more of the hypervariable region residues of the parent antibody will have been substituted, e.g. from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e. same residue) or similar (i.e. amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen such as C3b or a fragment thereof. One or more of the antibody mutants selected from this initial screen are optionally subjected to one or more further biological activity assays to confirm that the antibody mutant(s) with enhanced binding affinity are indeed useful, e.g. for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Further details of the preparation, selection, enrichment and affinity maturation of C3b antibodies by phage display are provided in the Examples below.

Recombinant Production of C3b Antibodies

The anti-C3b antibodies of the invention can be produced recombinantly, using techniques and materials readily obtainable.

For recombinant production of an anti-C3b antibody, the nucleic acid encoding it is isolated and inserted into a replicable vector for further cloning (amplification of the DNA) or for expression. DNA encoding the antibody is readily isolated or synthethized using conventional procedures (e.g., by using oligonucleotide probes that are capable of binding specifically to DNAs encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

(i) Signal Sequence Component

The antibody of this invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process the native antibody signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the antibody.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity.

Alternatively, host cells (particularly wild-type hosts that contain endogenous DHFR) transformed or co-transformed with DNA sequences encoding antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al. (1979) *Nature* 282:39). The trp1 gene provides a selection marker for a mutant strain of yeast lacking the ability to grow in tryptophan, for example, ATCC No. 44076 or PEP4-1. Jones (1977) *Genetics* 85:12. The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg (1990) *Bio/Technology* 8:135. Stable multi-copy expression vectors for secretion of mature recombinant human serum albumin by industrial strains of *Kluyveromyces* have also been disclosed. Fleer et al. (1991) *Bio/Technology* 9:968-975.

(iv) Promoter Component

Expression and cloning vectors usually contain a promoter that is recognized by the host organism and is operably linked to the antibody nucleic acid. Promoters suitable for use with prokaryotic hosts include the phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al. (1982) *Nature* 297:598-601 on expression of human β-interferon cDNA in mouse cells under the control of a thymidine kinase promoter from herpes simplex virus. Alternatively, the rous sarcoma virus long terminal repeat can be used as the promoter.

(v) Enhancer Element Component

Transcription of a DNA encoding the antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv (1982) *Nature* 297:17-18 on enhancing elements for activation of eukaryotic promoters. The enhancer may be spliced into the vector at a position 5' or 3' to the antibody-encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as

*B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. (1977) *J. Gen Virol.* 36:59); baby hamster kidney cells (BHK, ATCC CCL 10); Chinese hamster ovary cells/-DHFR (CHO, Urlaub et al. (1980) *Proc. Natl. Acad. Sci. USA* 77:4216); mouse sertoli cells (TM4, Mather (1980) *Biol. Reprod.* 23:243-251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al. (1982) *Annals N.Y. Acad. Sci.* 383:44-68); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce the antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. (1979) *Meth. Enz.* 58:44, Barnes et al. (1980) *Anal. Biochem.* 102:255, U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCINT™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Antibody Purification

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al. (1992) *Bio/Technology* 10:163-167 describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al. (1983) *J. Immunol. Meth.* 62:1-13). Protein G is recommended for all mouse isotypes and for human γ3 (Guss et al. (1986) *EMBO J.* 5:15671575). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Screening Assays and Animal Models for Identifying C3b Antibodies and Other C3b Antagonists C3b antibodies and other C3b antagonists can be evaluated in a variety of in vitro and in vivo assays for their ability to selectively inhibit the alternative complement pathway and to prevent and treat complement-associate disorders.

In vitro assays, such as binding and competitive binding assays, hemolytixc assays are described in the Examples.

The in vivo therapeutic activity of the C3b antagonists, such as C3b antibodies, herein can be tested in relevant animal models. Thus, for example, recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al. *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 623-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues.

Recombinant (transgenic) animal models can be engineered by introducing the coding portion of the genes of interest into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and other monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cell. Biol.* 3, 1803-1814 [1983]); sperm-mediated gene transfer (Lavitrano et al., *Cell* 57, 717-73 [1989]). For review, see, for example, U.S. Pat. No. 4,736,866.

Efficacy in the prevention and/or treatment of arthritis can, for example, be evaluated in a collagen-induced arthritis model (Terato et al. *Brit. J. Rheum.* 35:828-838 (1966)). Potential arthritis prophylactics/therapeutics can also be screened in a model of antibody-mediated arthritis induced by the intravenous injection of a cocktail of four monoclonal antibodies, as described by Terato et al., *J. Immunol.* 148: 2103-8 (1992), and Terato et al., *Autoimmunity* 22:137-47 (1995). Candidates for the prevention and/or treatment of arthritis can also be studied in transgenic animal models, such as, for example, TNF-α transgenic mice (Taconic). These animals express human tumor necrosis factor (TNF-α), a cytokine which has been implicated in the pathogenesis of human rheumatoid arthritis. The expression of TNF-α in these mice results in severe chronic arthritis of the forepaws and hind paws, and provides a simple mouse model of inflammatory arthritis.

In recent years, animal models of psoriasis have also been developed. Thus, Asebia (ab), flaky skin (fsn), and chronic proliferative dermatitis (cpd) are spontaneous mouse mutations with psoriasis-like skin alterations. Transgenic mice with cutaneous overexpression of cytokines, such as interferon-γ, interleukin-1a, keratinocyte growth factor, transforming growth factor-α, interferon-6, vascular endothelial growth factor, or bone morphogenic protein-6, can also be used to study in vivo psoriasis and to identify therapeutics for the treatment of psoriasis. Psoriasis-like lesions were also described in $β_2$-integrin hypomorphic mice backcrossed to the PL/J strain and in $β_1$-integrin transgenic mice, scid/scid mice reconstituted with CD4$^+$/CD45RB$^{hi}$ T lymphocytes as well as in HLA-B27/h$β_2$m transgenic rats. Xenotransplantation models using human skin grafted on to immunodeficient mice are also known. Thus, the antibodies and other C3b antagonists of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path.* (1995) 146:580. For further details see, e.g. Schon, M. P., *J Invest Dermatology* 112:405-410 (1999).

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test CRIg and CRIg agonists for activity and effectiveness in the treatment of asthma are described by Wolyniec, W. W. et al, *Am. J. Respir. Cell Mol. Biol.* (1998) 18:777 and the references cited therein.

Contact hypersensitivity is a simple in vivo assay of cell mediated immune function. In this procedure, epidermal cells are exposed to exogenous haptens which give rise to a delayed type hypersensitivity reaction which is measured and quantitated. Contact sensitivity involves an initial sensitizing phase followed by an elicitation phase. The elicitation phase occurs when the epidermal cells encounter an antigen to which they have had previous contact. Swelling and inflammation occur, making this an excellent model of human allergic contact dermatitis. A suitable procedure is described in detail in *Cur-* rent Protocols in Immunology, Eds. J. E. Cologan, A. M. Kruisbeek, D. H. Margulies, E. M. Shevach and W. Strober, John Wiley & Sons, Inc., 1994, unit 4.2. See also Grabbe, S, and Schwarz, T, *Immun. Today* 19(1):37-44 (1998).

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, supra, unit 4.3.

An animal model for skin allograft rejection is a means of testing the ability of T cells to mediate in vivo tissue destruction which is indicative of and a measure of their role in anti-viral and tumor immunity The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, supra, unit 4.4. Other transplant rejection models which can be used to test CRIg and CRIg agonists are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. CRIg and its agonists and antagonists can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

Models of myocardial ischemia-reperfusion can be performed in mice or rats. Animals are tracheostomized and ventilated with a small animal ventilator. Polyethylene catheters are placed in the internal carotid artery and the external jugular vein for measurement of mean arterial blood pressure. Myocardial ischemia reperfusion is initiated by ligating the left anterior descending artery (LAD) with a 6-O suture. Ischemia is produced by tightening the reversible ligature around the LAD to completely occlude the vessel. The ligature is removed after 30 min and the heart perfused for 4 hours. CRIg and CRIg agonists can be tested for their efficacy by measuring heart infarct size, heart creatine kinase activity, myeloperoxidase activity and immunohistochemistry using anti C3 antibodies.

A model of diabetic retinopathy involves treatment of mice or rats with streptozotocin. CRIg and CRIg agonists can be tested on their effect on venule dilatation, intraretinal microvascular abnormalities, and neovascularization of the retina and vitreous cavity.

A model for membranoproliferative glomerulonephritis can be established as follows: Female mice are immunized i.p. with 0.5 mg control rabbit IgG in CFA (day-7). Seven days later (day 0), 1 mg of the rabbit anti-mouse glomerular basement membrane (GBM) antibody is injected i.v. via the tail vein. Elevation of anti-rabbit IgG antibody in the serum is measured by ELISA. 24-h urine samples are collected from the mice in metabolic cages, and mouse renal function is assessed by the measurement of urinary protein in addition to blood urea nitrogen.

An animal model of age-related macular degeneration (AMD) consists of mice with a null mutation in Ccl-2 or Ccr-2 genes. These mice develop cardinal features of AMD, including accumulation of lipofuscin in and drusen beneath the retinal pigmented epithelium (RPE), photoreceptor atrophy and choroidal neovascularization (CNV). These features develop beyond 6 months of age. CRIg and CRIg agonists can be tested for the formation of drusen, photoreceptor atrophy and choroidal neovascularization.

CNV can be tested in various models of laser-induced choroidal neovascularization. Thus, for example CNV can be induced in rats and cynomolgus monkeys by intense laser photocoagulation, which results in choroidal neovascularization. Progress and treatment of this condition can be evaluated, e.g. by fluorescein angiography, histopathologic and immunohistochemical evaluation, and by pharmacokinetics, hemolytic, antibody screening and complement activation assays of serum collected from the animals before and after treatment, in different time intervals. Efficacy of preventative administration can be monitored by similar methods, including monitoring of vascular leakage by fluorescein angiography, inhibition of complement deposition at the site of laser burn, ocular exam, ocular photography, harvest of vitreous and retinal tissue, and the like. Further details are provided in the examples below.

Treatment Methods

For the prevention, treatment or reduction in the severity of a complement-associated disorder, the appropriate dosage of a compound of the invention will depend on the type of disorder to be treated, as defined above, the severity and course of the disorder, whether the agent is administered for preventive or therapeutic purposes, previous therapy, the patient's clinical history and response to the compound, and the discretion of the attending physician. The compound is suitably administered to the patient at one time or over a series of treatments. Preferably, it is desirable to determine the dose-response curve and the pharmaceutical composition of the invention first in vitro, and then in useful animal models prior to testing in humans.

For example, depending on the type and severity of the disease, about 1 µg/kg to 15 mg/kg (e.g. 0.1-20 mg/kg) of an anti-C3b antibody or other C3b antagonist is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

The efficacy of the treatment of complement-associated eye conditions, such as AMD or CNV, can be measured by various endpoints commonly used in evaluating intraocular diseases. For example, vision loss can be assessed. Vision loss can be evaluated by, but not limited to, e.g., measuring by the mean change in best correction visual acuity (BCVA) from baseline to a desired time point (e.g., where the BCVA is based on Early Treatment Diabetic Retinopathy Study (ET-DRS) visual acuity chart and assessment at a test distance of 4 meters), measuring the proportion of subjects who lose fewer than 15 letters in visual acuity at a desired time point compared to baseline, measuring the proportion of subjects who gain greater than or equal to 15 letters in visual acuity at a desired time point compared to baseline, measuring the proportion of subjects with a visual-acuity Snellen equivalent of 20/2000 or worse at a desired time point, measuring the NEI Visual Functioning Questionnaire, measuring the size of CNV and amount of leakage of CNV at a desired time point, e.g., by fluorescein angiography, etc. Ocular assessments can be done, e.g., which include, but are not limited to, e.g., performing eye exam, measuring intraocular pressure, assessing visual acuity, measuring slitlamp pressure, assessing intraocular inflammation, etc.

Pharmaceutical Compositions

The C3b antibodies and other C3b antagonists of the present invention can be administered for the treatment of complement-associated disorders in the form of pharmaceutical compositions.

Therapeutic formulations of a C3b antibody or other antagonist of the invention, are prepared for storage by mixing the active molecule having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Lipofections or liposomes can also be used to deliver the polypeptide, antibody, or an antibody fragment, into cells. Where antibody fragments are used, the smallest fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889-7893 [1993]).

The active molecules may also be entrapped in microcapsules prepared, for example, by coascervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37 C, resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The compounds of the invention for prevention or treatment of an ocular disease or condition are typically administered by ocular, intraocular, and/or intravitreal injection. Other methods administration by also be used, which includes but is not limited to, topical, parenteral, subcutaneous, intraperitoneal, intrapulmonary, intranasal, and intralesional administration. Parenteral infusions include intramuscular, intravenous, intraarterial, intraperitoneal, or subcutaneous administration.

Formulations for ocular, intraocular or intravitreal administration can be prepared by methods and using ingredients known in the art. A main requirement for efficient treatment is proper penetration through the eye. Unlike diseases of the front of the eye, where drugs can be delivered topically, retinal diseases require a more site-specific approach. Eye drops and ointments rarely penetrate the back of the eye, and the blood-ocular barrier hinders penetration of systemically administered drugs into ocular tissue. Accordingly, usually the method of choice for drug delivery to treat retinal disease, such as AMD and CNV, is direct intravitreal injection. Intravitrial injections are usually repeated at intervals which depend on the patient's condition, and the properties and half-life of the drug delivered. For intraocular (e.g. intravitreal) penetration, usually molecules of smaller size are preferred.

The following examples are offered for illustrative purposes only, and are not intended to limit the scope of the present invention in any way.

Commercially available reagents referred to in the examples were used according to manufacturer's instructions unless otherwise indicated. The source of those cells identified in the following examples, and throughout the specification, by ATCC accession numbers is the American Type Culture Collection, 10801 University Boulevard, Manassas, Va. 20110-2209.

Amino acid residues within antibody amino acid sequences are numbered according to Kabat (Kabat et al., *Sequences of proteins of immunological interest*, 5th Ed., Public Health Service, National Institutes of Health, Bethesda, Md. (1991)). Single letter amino acid abbreviations are used. DNA degeneracies are represented using the IUB code (N=A/C/G/T, D=A/G/T, V=A/C/G, B=C/G/T, H=A/C/T, K=G/T, M=A/C, R=A/G, S=G/C, W=A/T, Y=C/T).

EXAMPLE 1

Antibodies derived from phage encoding hypervariable regions of a starting antibody The nucleic acid sequences of the VL and VH domains of the HERCEPTIN® anti-HER2 antibody rhuMAB 4D5-8 (Genentech, Inc.) (FIGS. 18A and 18B) were used as the starting sequence for mutagenesis of the HVRs and phage selection for binding to human C3b. Antibody 4D5 is a humanized antibody specific for a cancer-associated antigen known as Her-2 (erbB2). The antibody includes variable domains having consensus framework regions, where a few positions were reverted to mouse sequence during the process of increasing affinity of the humanized antibody. The sequence and crystal structure of humanized antibody 4D5 have been described in U.S. Pat. No. 6,054,297, Carter et al, PNAS 89:4285 (1992), the crystal structure is shown in Carter et al., *J. Mol. Biol.* 229:969 (1993) and online at www/ncbi/nih/gov/structure/mmdb(MMDB#s-990-992), the entire disclosures of which are hereby expressly incorporated by reference.

The HERCEPTIN® VL and VH domains comprises the consensus human kappa I VL domain and a variant of the human subgroup III consensus VH domain. The variant VH domain has 3 changes from the human consensus: R71A, N73T and L78A.

The phagemid used for this work was a monovalent Fab-g3 display vector (pV0350-2B) having 2 open reading frames under control of the phoA promoter, essentially as described in Lee et al., *J. Mol. Biol.* (2004), 340(5):1073-93. The first open reading frame consists of the stII signal sequence fused to the VL and CH1 domains acceptor light chain and the second consists of the stII signal sequence fused to the VH and CH1 domains of the acceptor heavy chain followed by a truncated minor phage coat protein P3. See Lee et al., supra.

Antibodies Generated by Mutagenesis of Heavy Chain HVRs

Fab clone YW 144.2.43 was generated by mutagenesis of HVR-H1, H2, and H3 of huMAb 4D5-8 (HERCEPTIN® anti-HER2 antibody, Genentech, Inc.) heavy chain and selection against human C3b fusion protein. In HVR-H1, Kabat positions 26 (G), 27 (F), 28 (T), 29 (I), 34 (I), and 35 (H) were held constant, and the amino acids at positions 30-33 were varied. In HVR-H2, Kabat positions 51 (I), 52a (P), 55 (G), 57 (T), 59 (Y), 60 (A), 61 (D), 62 (S), 63 (V), 64 (K), and 65 (G) were held constant, and positions 49, 50, 52, 53, 54, 56, and 58 were varied. In HVR-H3, Kabat positions 93 (A) and 102 (Y) were held constant, and positions 94-100, 100a-h, and 101 were varied. The light chain of YW 144.2.43 was the modified huMAb 4D5-8 sequence (modified at positions 30, 66 and 91), the HVRs of which were not varied during phage selection. Sequence diversity was introduced into each hypervariable region by mutagenesis of selected amino acid positions using standard mutagenesis techniques.

Generation of Phage Libraries

Randomized oligonucleotide pools designed for each hypervariable region were phoshorylated separately in six 20 µl reactions containing 660 ng of oligonucleotide, 50 mM Tris pH 7.5, mM MgCl$_2$, 1 mM ATP, 20 mM DTT, and 5 U polynucleotide kinase for 1 h at 37° C. The six phosphorylated oligonucleotide pools were then combined with 20 µg of Kunkel template in 50 mM Tris pH 7.5, 10 mM MgCl$_2$ in a final volume of 500 µl resulting in an oligonucleotide to template ratio of 3. The mixture was annealed at 90° C. for 4 min, 50° C. for 5 min and then cooled on ice. Excess, unannealed oligonucleotide was removed with a QIAQUICK™ PCR purification kit (Qiagen kit 28106) using a modified protocol to prevent excessive denaturation of the annealed DNA. To the 500 µl of annealed mixture, 150 µl of PB was added, and the mixture was split between 2 silica columns. Following a wash of each column with 750 µl of PE and an extra spin to dry the columns, each column was eluted with 110 µl of 10 mM Tris, 1 mM EDTA, pH 8. The annealed and cleaned-up template (220 µl) was then filled in by adding 1 µl 100 mM ATP, 10 µl 25 mM dNTPs (25 mM each of dATP, dCTP, dGTP and dTTP), 15 µl 100 mM DTT, 25 µl 10×TM buffer (0.5 M Tris pH 7.5, 0.1 M MgCl$_2$), 2400 U T4 ligase, and 30 U T7 polymerase for 3 h at room temperature.

The filled in product was analyzed on Tris-Acetate-EDTA/agarose gels (Sidhu et al., *Methods in Enzymology* 328:333-363 (2000)). Three bands were usually visible: the bottom band is a correctly filled and ligated product, the middle band is a filled but unligated product, and the top band is a strand displaced product. The top band is produced by an intrinsic side activity of T7 polymerase and is difficult to avoid (Lechner et al., *J. Biol. Chem.* 258:11174-11184 (1983)); however, this band transforms 30-fold less efficiently than the bottom band and usually contributes little to the library. The middle band is due to the absence of a 5' phosphate for the final ligation reaction; this band transforms efficiently and gives mainly wild type sequence.

The filled in product was then purified and electroporated into SS320 cells and propagated in the presence of M13/KO7 helper phage as described by Sidhu et al., *Methods in Enzymology* 328:333-363 (2000). Library sizes ranged from 1-2× 10$^9$ independent clones. Random clones from the initial libraries were sequenced to assess library quality.

Phage Selection

The human C3b proteins were used as the selection antigens. Human C3b was coated on MaxiSorp microtiter plates (Nunc) at 10 µg/ml in PBS and incubated overnight at 4 degrees. For the first round of selection 12 wells of target were used. Wells were blocked for 1 h at RT using Phage Blocking Buffer (1% BSA, 0.05% Tween 20, PBS). Phage libraries were PEG precipitates from frozen glycerol stocks, resuspended in Phage Blocking Buffer and incubated for 1 hr, at RT. Phage libraries were then added to the blocked antigen plates incubated overnight at RT. After overnight binding, unbound/non-specific phage were removed from the antigen plates by washing with Wash Buffer (PBS, 05% Tween20. Bound phage were eluted by incubating the wells with 50 mM HCl, 0.5 M KCl for 30 min. Phage were amplified using XL-1 Blue cells and M13/KO7 helper phage and grown for 36 hrs at 30° C. in 2YT, 50 µg/ml carbanecillin, 50 µg/ml kanamycin, 10 ug/ml tetracycline. Amplified phage were then recovered using a modified PEG precipitation protocol (Monaci, P., Cortese, R., Screening phage libraries with sera, In: *Phage display—A practical approach*, Clackson and Lowman, eds., 2004, pp. 193-215). The titers of phage eluted from a target coated well were compared to titers of phage recovered from a non-target coated well to assess enrichment. Four rounds of phage selection were completed with the number of target wells decreasing to 4 (round 2) and 2 (rounds 3&4). Casein Blocking Buffer (Pierce) was used as the blocking reagent for antigen plates and phage for rounds 2 & 4. Selection rounds 2-4 used a 3-4 hour phage-antigen binding period and increased washing stringency. In the case of human C3b panning, human C3 was also added (>1 μM) in selection rounds 2-4 during phage-antigen incubation as counter select against phage antibodies that could also bind human C3. Human phage clone YW144.2.43 was selected. The C3b panning results are shown in FIG. 1. The C3b binding characteristics were determined as disclosed in Example 3.

EXAMPLE 2

Antibodies generated by variation of HVRs H1, H2, H3 and L3

Clone YW144.2.43 was generated by mutagenesis of HVR-H1, H2, H3 and L3 of huMAb 4D5-8 (HERCEPTIN® anti-HER2 antibody, Genentech, Inc.) heavy chain variable domain and huMAb 4D5-8 modified light chain variable domain. In HVR-H1, Kabat positions 26 (G), 28 (T), 29 (F), 30 (S), 31 (S), and 35 (S) were held constant, and the amino acids at positions 27, 32-34 were varied. In HVR-H2, Kabat positions 49 (S), 51 (I), 55 (G), 57 (T), 59 (Y), 60 (A), 61 (D), 62 (S), 63 (V), 64 (K), and 65 (G) were held constant, and positions 50, 52, 52a, 53, 54, 56, and 58 were varied. In HVR-H3, Kabat positions 93 (A), 94 (R), 100f-g (deletion) were held constant, and positions 95-100, 100a-e, 100h, and 102 were varied. In HVR-L3, Kabat positions 89 (O), 90 (O), 95 (P) and 97 (T) were held constant, and positions 91-94 and 96 were varied. The sequence of HVR-L1 was held constant as RASQSISSYLA (SEQ ID NO:11) and the sequence of HVR-L2 was held constant as GASSRAS (SEQ ID NO:12). Sequence diversity was introduced into each hypervariable region by mutagenesis of selected amino acid positions using standard mutagenesis techniques. Anti-C3v antibody clones were selected and sequenced.

Affinity Maturation of YW144.2.43

To improve the affinity of anti-C3b antibody YW144.2.43, three phage display libraries were generated in the background of YW144.2.43, each targeting a multiple HVRs for soft randomization mutagenesis as described in Lee et al., *J. Mol. Biol.* (2004), 340(5):1073-93. To avoid re-selecting YW144.2.43 from a potential high background of template, stop codons were introduced into the HVR to be mutated prior to generating each library. A solution sorting method was used to enhance the efficiency of the affinity-based phage selection process. By manipulating the biotinylated target concentration, reducing the phage capture time to lower backgrounds and the addition of unbiotinylated target to eliminate clones with faster off rates, high affinity clones can be proficiently selected. Lee et al., *J. Mol. Biol.* (2004), 340(5):1073-93. From the first round of selection, enrichment (target dependent phage capture) was observed suggesting a large number of clones were present in each library with reasonably high affinity for human C3b. Selection stringency was increased in subsequent rounds. After 5 rounds of selection, clones from each library were analyzed. New sequences were observed in libraries targeting each of the six HVRs. Selected clones were screened by phage ELISA and then expressed as IgG protein and their affinity characterized using Biacore™ binding analysis.

Phage libraries of affinity matured clones were sorted using a solid/solution sorting method. Human C3b was biotinylated by mixing 500 μl of 3.6 mg/ml human C3b in PBS, and 10 μl of 1 M potassium phosphate, pH 8 with 20 μl 4 mM Sulfo-NHS-LC-biotin (Pierce). For the 1st round of selection, biotinylated C3b was coated on MaxiSorp microtiter plates (Nunc) at 10 μg/ml in PBS and incubated overnight at 4 degrees. For the first round of selection 16 wells of target were used. Wells were blocked for 1 h at RT using SuperBlock (Pierce). Maturation phage libraries were diluted in SuperBlock buffer and incubated 1 hr. at RT. Phage libraries were then added to the blocked antigen plates incubated 2 hrs. at RT. After binding, unbound/non-specific phage were removed from the antigen plates by washing with Wash Buffer (PBS, 0.5% Tween20. Bound phage were eluted by incubating the wells with 50 mM HCl, 0.5 M KCl for 30 min. Phage were amplified using XL-1 Blue cells and M13/KO7 helper phage and grown for 36 hrs at 30° C. in 2YT, 50 μg/ml carbanecillin, 50 ug/ml kanamycin, 10 ug/ml tetracycline. Amplified phage were then recovered using a modified PEG precipitation protocol (Monaci, P., Cortese, R., supra). The titers of phage eluted from a target coated well were compared to titers of phage recovered from a non-target coated well to assess enrichment. For selection rounds 2-5 a solution sorting protocol was implemented. Microtiter wells were coated with 10 μg/ml neutravidin in PBS overnight at 4° C. and then blocked for 1 h using SuperBlock (Pierce). Recovered phage libraries were suspended in SuperBlock were mixed with 50 nM b-Robo4-His for 1 hr. Phage bound to b-C3b were captured on neutravidin coated wells for 30 min and unbound phage were washed away with Wash Buffer. Phage were eluted using 50 mM HCl, 500 mM KCl for 30 min, neutralized, and propagated in XL1 blue cells (Stratagene) in the presence of KO7 helper phage (New England Biolabs). Subsequent rounds of sorting were performed similarly with the following exceptions: in round 2 the final b-C3b concentration was 50 nM, in round 3 the final b-C3b concentration was 25 nM, in round 4 the final b-C3b concentration was 5 nM and in round 5 the final b-C3b concentration was 0.5 nM with 50 nM of unbiotinylated C3b added to the mixture for 1 h prior to capture on neutravidin.

Several affinity matured clones were selected for binding to human C3b and sequenced. The amino acid sequences of the heavy and light chain Fab fragments of affinity matured antibody YW 144.2.43.S77 (briefly, S77) are shown in FIG. 5.

EXAMPLE 3

Characterization of selected anti-C3b antibody clone

Phage ELISA—Phage competition binding assays were performed to determine the approximate binding affinity (determined as phage $IC_{50}$) of phage-displayed Fabs for C3b. The assays were performed as follows. Purified phage supernatants from each clone were produced using a modified PEG precipitation protocol as described above. Purified phage supernatants were serially diluted in Phage Blocking buffer, then incubated on plates coated with C3b (1 μg/ml) for 15 minutes. The plates were washed with Wash Buffer and were incubated for 30 minutes with horseradish peroxidase/anti-M13 antibody conjugate (diluted 1:5000 in PBS buffer) (Amersham Pharmacia Biotech). The plates were washed, developed with tetramethylbenzidine (TMB) substrate (Kirkegaard and Perry Laboratories) and quenched with 0.1N HSO4. Absorbance was measured spectrophotometrically at 450 nm to determine the phage concentration giving about 50% of the signal at saturation. A fixed, sub-saturating concentration of phage was diluted in Phage Blocking buffer containing two-fold serial dilutions of C3b protein from 350 nM C3b to 5 nM C3b. The mixtures were incubated for one hour with gentle shaking at room temperature, transferred to plates coated with C3b (1 µg/ml) and the plates were incubated for 20 minutes. The plates were washed and treated as above. The binding affinities were estimated as $IC_{50}$ values (defined as the concentration of antigen that blocked 50% of the phage binding to the immobilized antigen). The C3b phage competition results are shown in FIG. 2.

IgG production and affinity determination—To express IgG protein for affinity characterization, a stop codon was introduced between the heavy chain and g3 in the phage display vector. Clones were transformed into *E. coli* 34B8 cells and grown in AP5 media at 30 C (Presta et al. *Cancer Res.* 57: 4593-4599 (1997)). Cells were harvested by centrifugation, suspended in 10 mM Tris, 1 mM EDTA pH 8 and broken open using a microfluidizer. Fab was purified with Protein G affinity chromatography.

Figure 7:
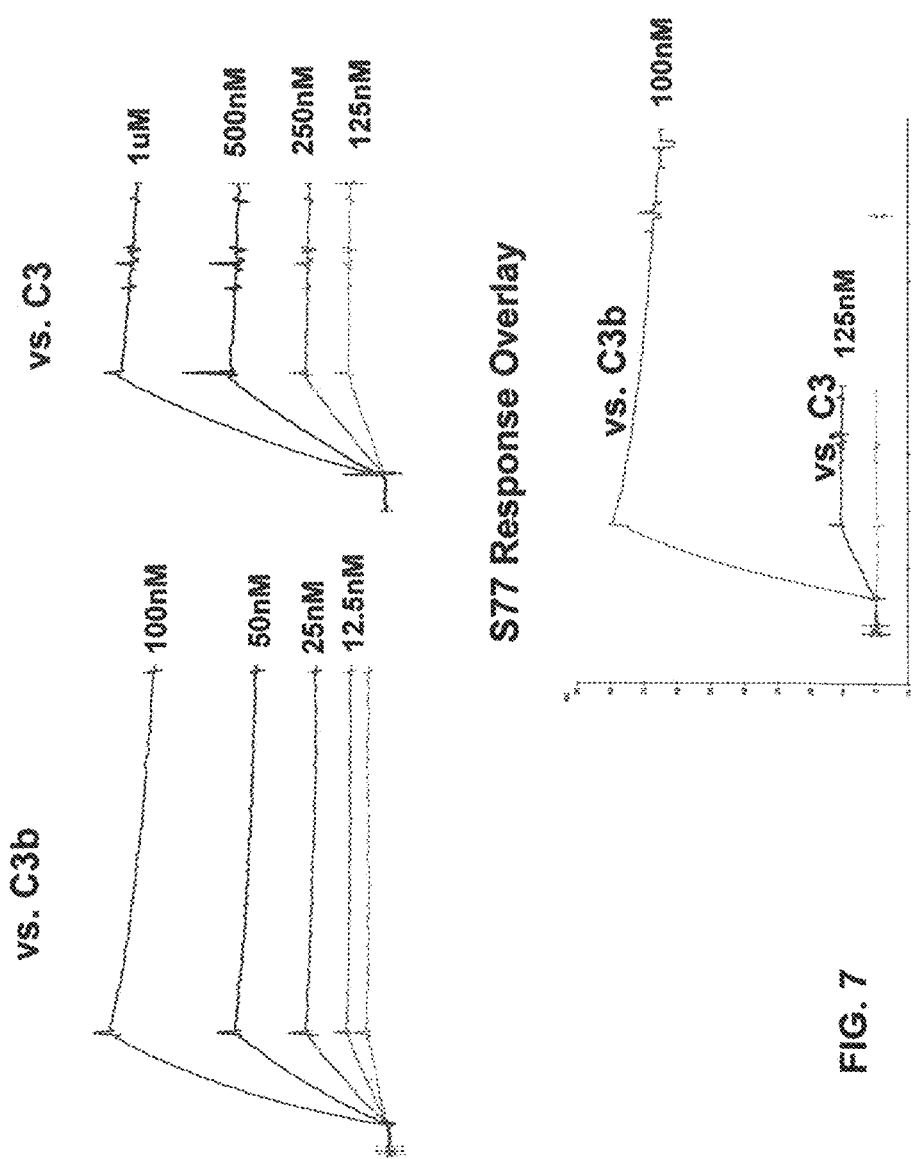
FIG. 7. SPR sensograms and S77 binding affinity to C3 and C3b.

The binding affinity of the phage-derived anti-C3b antibody YW144.2.43 and its affinity matured variant YW144.2.43S77 (Fab fragments) for human C3b and C3 was determined by surface plasmon resonance measurement using a BIACORE® 3000 system (Biacore, Inc., Piscataway, N.J.). The antibody Fab fragments tested were YW144.2.43 and YW144.2.43S7. Briefly, flow cells 1 and 2 on carboxymethylated dextran biosensor chips (CMS, Biacore Inc.) were activated with 0.2 M N-ethyl-N'-(3-dimethylaminopropyl)-carbodiimide hydrochloride (EDC) and 0.05 M N-hydroxysuccinimide (NHS) at a flow rate of 5 µl/in for 7 min. Flow cell one was left uncoated as negative control. These activated chips were coated with anti-C3b Fab by dilution to 5 µg/ml with 10 mM sodium acetate, pH 4.8, before injection at a flow rate of 5 µl/minute to achieve approximately 50 response units (RU) of coupled antibody. Next, 1M ethanolamine was injected to block unreacted groups. For kinetics measurements, two-fold serial dilutions of human C3b or C3 soluble antigen (approximately 100 nM to approximately 3 nM for C3b, ~1 µM to 50 nM for C3) were injected in PBS with 0.05% Tween 20 at 25° C. at a flow rate of 35 µl/min. After each injection the chip was regenerated using 20 mM HCl. Binding response was corrected by subtracting the RU from a blank flow cell. Association rates ($k_{on}$) and dissociation rates ($k_{off}$) were calculated using a simple one-to-one Langmuir binding model (BIAevaluation Software version 3.2). The equilibrium dissociation constant ($K_D$) was calculated as the ratio $k_{dissociation}/k_{association}$. The binding affinities are shown in FIGS. 6 and 7.

In another experiment, purified C3b or C3 were captured in microtiter plates using a polyclonal C3 antibody. Binding of S77 (A) or a polyclonal anti C3 antibody (B) to captured C3b or C3 was determined using a secondary HRPO-conjugated antibody. Color was developed with TMB (KPL), stopped in 2N $H_2SO_4$ and absorbance read at 450 nm C3b ELISA for testing specificity of anti C3b antibody S77. Twenty-five µL of capture antibody (YW144.2.45.577 Affinity Matured xC3/C3b (Genentech) 2 µg/ml) diluted in PBS was added to wells of a microtitre plate and incubated overnight at 4° C. The plate was washed 3x with wash buffer (PBS/0.05% Tween 20 (20x stock; Media Prep; Cat. A3355)). Fifty µL of block buffer was added to the wells and the plate incubated for 1-3 hours with gentle agitation (room temperature) and washed 3x with wash buffer. Standard stock (C3b, Complement Technology Inc.; Cat. A114, stored at 100x in −20° C.) was prepared in Magic Buffer (1xPBS pH 7.4, 0.5% BSA, 0.05% Tween 20, 0.2% BgG, 15 PPM Proclin (Media Prep; Cat. A3381)+0.35M NaCl. Magic Buffer+0.35M NaCl is also used to prepare samples for analysis. Twentyfive µL of standards/samples is added to designated wells. Samples were incubate for ~2 hours (+/−0.5 hr) at RT with gentle agitation and washed 3x with wash buffer. The plate was turned 180 degrees and the wash step repeated. Detection antibody (Peroxidase Conj. Goat F(ab')$_2$ Anti-human C3 (Protos Immunoresearch; Cat. 765) was diluted 1:7K in Assay Diluent and incubated on the plate for 1-2 hours at RT with gentle agitation. The plate was washed 3x with wash buffer and turned 180 degrees with the wash step repeated. 50/50 TMB solution was made. ELISA plate was washed 3x with wash buffer. The plate was turned 180 degrees and the wash step repeated. 25 µL TMB was added to the wells. Color was developed at room temperature. Development time: 10 minutes for both plates. Color development was stopped by adding 25 µL 1.0M Phosphoric acid to wells. OD reading of plate was taken (450/630 nm). The results are shown in FIG. 8, panel A.

The total C3 used as a positive control for detection of C3 was carried out similarly to the C3b ELISA assay described above used to test specificity of S77 except that a goat IgG fraction to human C3 (Cappel 55033) was used as a capture antibody. The results are shown in FIG. 8, panel B.

Figure 8:
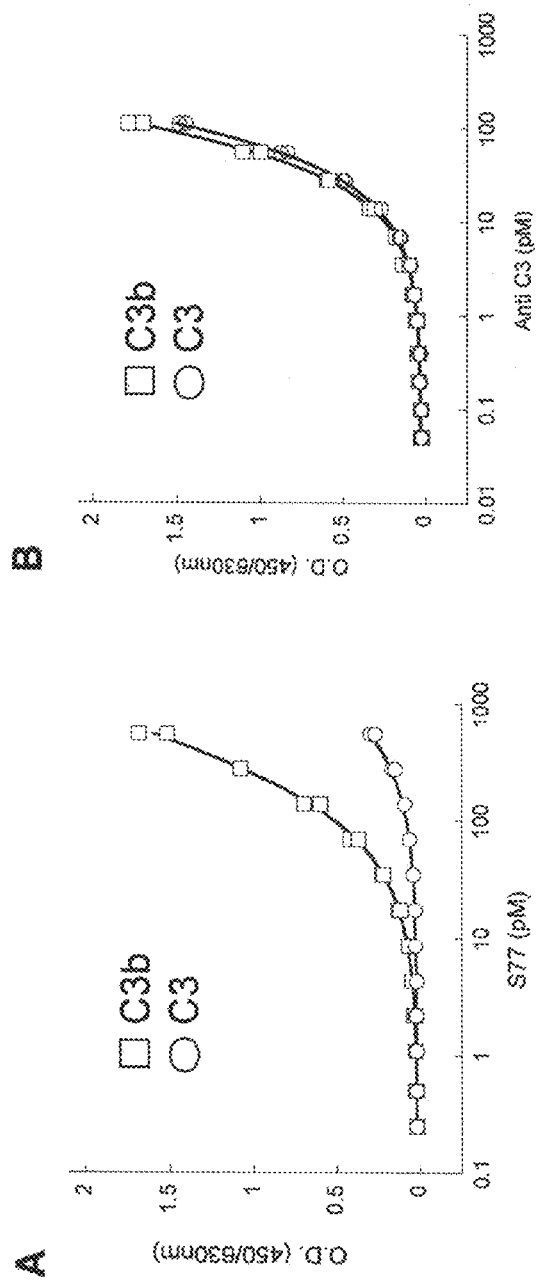
FIG. 8. S77 recognizes C3b, but not the pro-molecule C3. Purified C3b or C3 were captured in microtiter plates using a polyclonal C3 antibody. Binding of S77 (A) or a polyclonal anti C3 antibody (B) to captured C3b or C3 was determined using a secondary HRPO-conjugated antibody. Color was developed with TMB (KPL), stopped in 2N $H_2SO_4$ and absorbance read at 450 nm.

As shown in FIG. 8, S77 recognizes C3b, but not the pro-molecule C3.

EXAMPLE 4

C3b antibodies specifically inhibit the alternative pathway of complement

Hemolytic assay—For determining alternative pathway activity, rabbit erythrocytes (Er, Colorado Serum) were washed 3x in GVB and resuspended to $2 \times 10^9$/ml. Inhibitors (50 µl) and 20 µl of Er suspension were mixed 1:1 with GVB/0.1M EGTA/0.1M $MgCl_2$. Complement activation was initiated by the addition of C1q-depleted human serum (Quidel; 30 ul diluted 1:3 in GVB). After a 30 minute incubation at room temperature, 200 µl GVB/10 mM EDTA were added to stop the reaction and samples were centrifuged for 5 min at 500 g. Hemolysis was determined in 200 µl supernatant by measuring absorbance at 412 nm. Data were expressed as % of hemolysis induced in the absence of the inhibitor. To determine the effect of CRIg on the classical pathway of complement, a similar procedure was followed except that Er were replaced with IgM-coated sheep erythrocytes (E-IgM, CompTech) and the assay was performed in factor B deficient human serum in GVB++.

Figure 10:
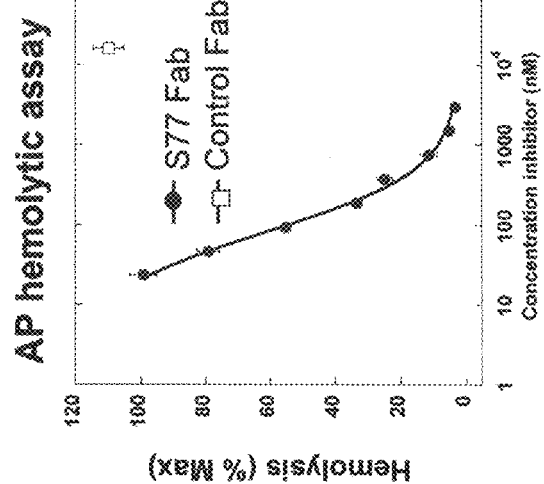
FIG. 10. Affinity-matured S77 Fab inhibits alternative pathway of complement.

As shown in FIGS. 9 and 10, affinity matured C3b antibody S77 specifically inhibits the alternative complement pathway and not the classical pathway.

EXAMPLE 5

C3b antibodies inhibit C5 binding to the C5 convertase

C5 competition assay—C3b was coated on a microtiter by incubation with 3 µg/ml C3b in PBS o/n at 4 C. The plate was blocked with 1% BSA in PBS and incubated with increasing concentrations of antibody mixed with 0.4 uM C5 in 20 mM Tris/20 mM Ca/20 mM Mg/150 mM NaCl/0.05% Tween/1% BSA. C5 binding was detected by incubation with anti-human C5 antibody (clone 7D12, Genentech) for 30 min @RT, followed by 1:5000 donkey-anti-mouse HRPO (Jackson).

Figure 11:
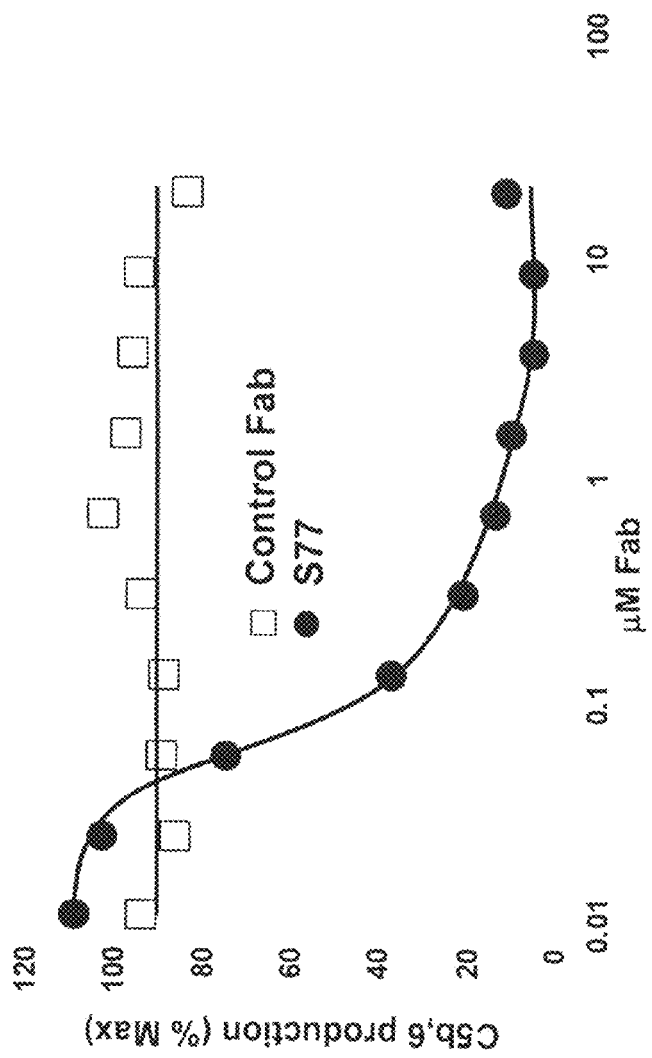
FIG. 11. C3b Fab (S77) inhibits C5 convertase. C5 convertase was performed as described (Rawal, N. and Pangburn, M. *J Immunol.* 2001 Feb. 15; 166(4):2635-42).
Figure 12:
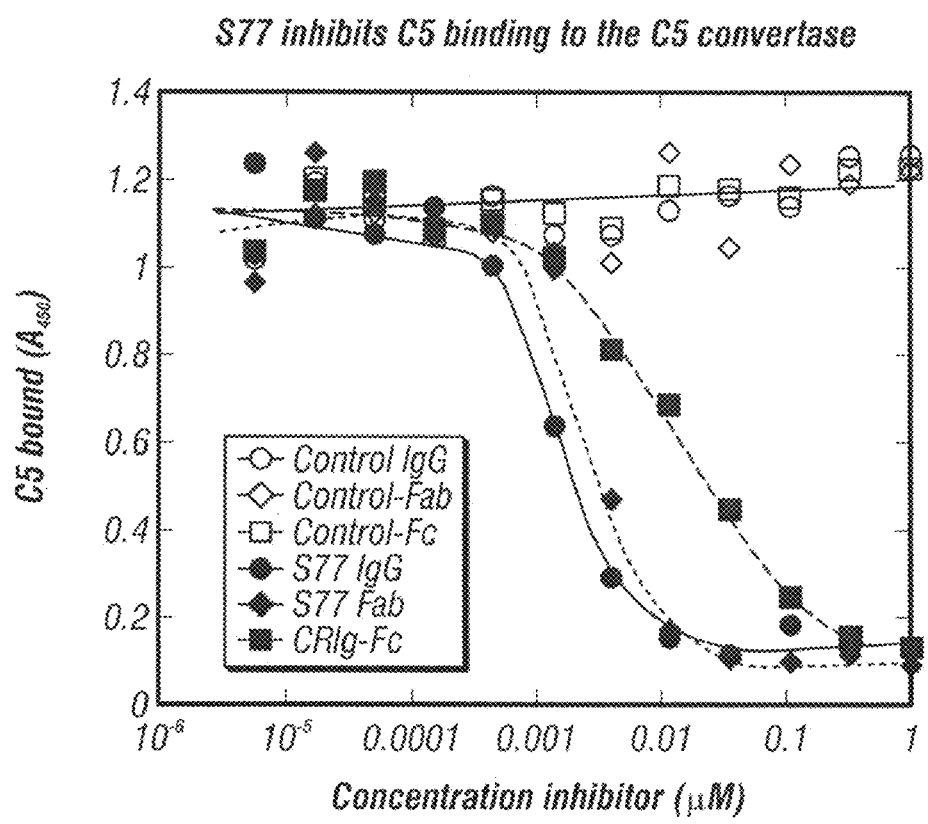
FIG. 12. IgG antibody S77 and its Fab fragment inhibit the C5 convertase by blocking binding of C5 to C3b, the non-catalytic subunit of the convertase. C5 in the presence of increasing concentrations of inhibitor was added to plates coated with C3b. C5 binding to the C3b multimers FIG. 13. S77 does not decay the convertase, in contrast to Factor H. A decay assay was performed by generation of a plate-coated C3 convertase in the presence of increasing concentrations of S77 or Factor H (positive control).

As shown in FIGS. 11 and 12, affinity matured C3b antibody S77 inhibits C5 convertase.

EXAMPLE 6

C3b antibodies do not display decay activity

Decay acceleration activity—Microtiter plates were coated overnight with 3 µg/ml C3b in PBS. Plates were washed 2 times in PBST (PBS/0.1%-Tween), blocked for 2 h at 37° C. with PBST containing 4% BSA. Plates were incubated for 2 hrs at room temperature in veronal buffer containing 400 ng/ml of factor B, 25 ng/ml of factor D, and 2 mM $NiCl_2$, 25 mM NaCl, 0.05% Tween 20 and 4% BSA followed by incubation for 15 min with factor H or S77 in PBST. Factor Bb was detected with sequential 1 hr incubations with 1:5,000 dilution of goat anti-human factor B polyclonal antibody (Kent) in PBST and 1:5,000 dilution of donkey anti-goat antibody conjugated to HRPO (Caltag) in PBST. Color was developed with TMB (KPL), stopped in 2N $H_2SO_4$ and absorbance read at 450 nm. Co-factor activity for factor I-mediated cleavage of C3b was measured by incubating 0.8 µM C3b and 80 nM factor I with 80 nM factor H or varying concentrations of S77 in 30 ml GVB. The mixture was incubated for 60 min at 37° C. and the samples analyzed by gel-electrophoresis as described for the C3 convertase assay.

Figure 13:
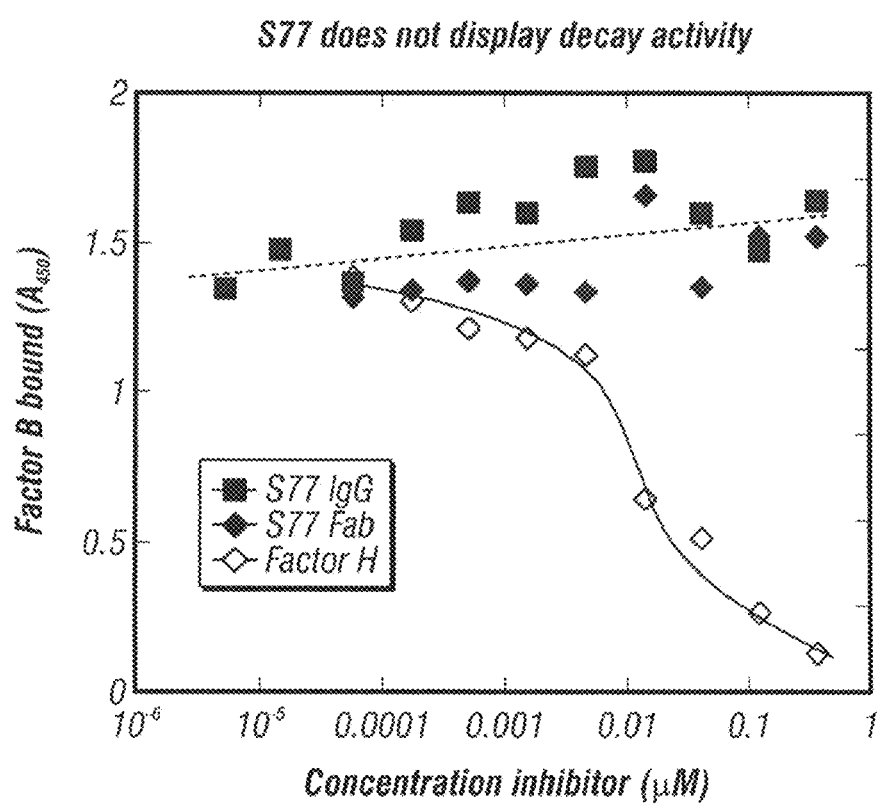

As shown in FIG. 13, S77 does not display decay acceleration activity.

EXAMPLE 7

S77 inhibits binding of pro-factor B to C3b and formation of C3bBb convertase Protocol MaxiSorp plate was coated for 4 hrs at RT with 3 µg/ml C3b (PUR13420) in PBS (20 µl/well). Wash was carried out 6× with 100 µl PBS 0.1% Tween (PBST) (BioTek EL405 washer). The plates were blocked 2 hrs at RT with 4% BSA/0.05% Tween/PBS, followed by shaking off the block into the sink. 20 µl AP convertase buffer was added for 2 hr at RT, followed by wash 6×PBST. 20 µl Abs were added for 45 min at RT, and the wells were washed 6×PBST. For detection of factor B/Bb, the wells were incubated with 1:7000 goat-anti-fB (Kent Labs) for 30 min at RT. For detection of S77 and CR1, PBST was added to the wells, which were then washed 6× with PBST, and incubated 30 min with 1:7,000 donkey-anti-goat IgG-HRPO (Jackson) in PBST++. Incubation 30 min at RT with 1:100 anti-6×-His (SEQ ID NO: 19) (R&D) in PBST++ was followed by wash 6×PBST. Developing was performed with 20 ml TMB substrate, and reaction stopped with 10 µl 2N sulfuric acid. Plate were read at 450 nm.

"AP Convertase Buffer": 4% BSA 0.1% Tween 20 2 mM NiCl2 25 mM NaCl 25 ng/mL factor D 400 ng/ml factor B (CompTech).

Following the above protocol, C3b was coated on microtiter plates. S77, a control Fab or CR1 fragment (LHRA-C) was added followed 1 hr later by addition of factor B. Binding of factor B to C3b was detected with a HRPO-conjugated secondary antibody, and absorbance read at 450 nm. The results are shown in FIG. 14, panel A.

Similarly, following the above protocol, C3b was coated on microtiter plates followed by addition of S77, a control Fab or a CR1 fragment (LHRA-C). A C3 convertase was generated by the addition of factor D and factor B. Convertase formation was determined using a primary antibody that recognizes factor Bb and a secondary HRPO-conjugated antibody. Color was developed with TMB (KPL), stopped in 2N $H_2SO_4$ and absorbance read at 450 nm. The results are shown in FIG. 14, panel B.

Figure 14:
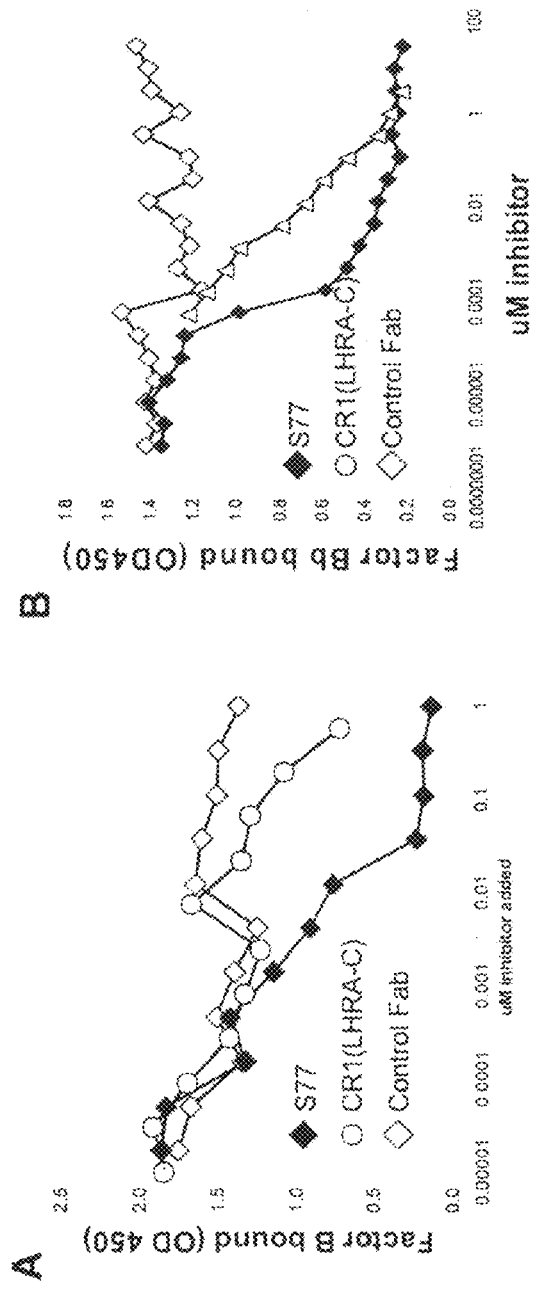
FIG. 14. S77 inhibits binding of pro-factor B to C3b, and inhibits formation of the C3bBb convertase.

As shown in FIG. 14, antibody S77 inhibits binding of pro-factor B to C3B, and inhibits formation of the C3bBb convertase.

EXAMPLE 8

S77 binds C3b in the presence of bound fBb and does not decay C3 convertase

Using the protocol described in Example 7, C3b was coated on microtiter plates. A C3 convertase was generated by the addition of factor D and factor B. S77, a control Fab or a CR1 fragment (LHRA-C) was added to the plate, and binding of these molecules was determined with secondary antibodies conjugated to HRPO. The results are shown in FIG. 15, panel A.

Similarly, following the protocol described in Example 7, microtiter plates were coated with 3 µg/ml C3b. Plates were incubated with factor B and factor D followed by incubation with CR1 (LHRA-C), S77 or control Fab. Factor Bb was detected with goat anti-human factor B and donkey anti-goat antibody conjugated to HRPO. Color was developed with TMB (KPL), stopped in 2N $H_2SO_4$ and absorbance read at 450 nm. The results are shown in FIG. 15, panel B.

Figure 15:
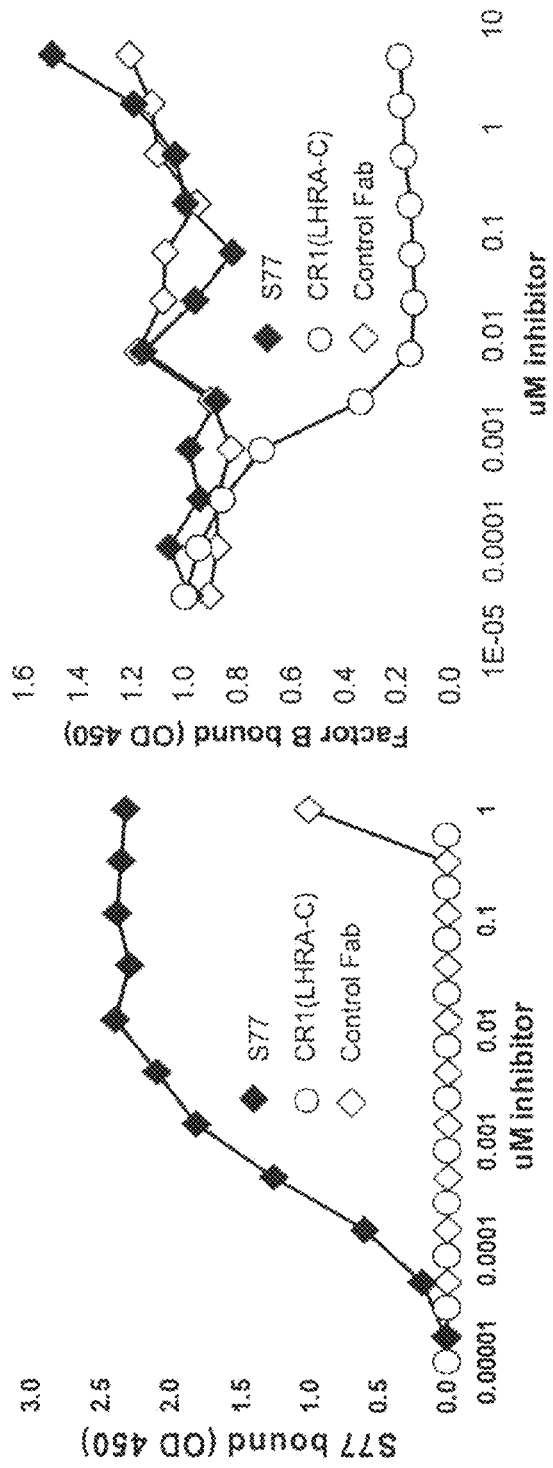
FIG. 15. S77 can bind C3b in the presence of bound fBb and does not decay the C3 convertase.

The results set forth in FIG. 15 show that S77 can bind C3b in the presence of bound fBb and does not decay the C3 convertase.

EXAMPLE 9

S77 inhibits factor h binding to c3b and inhibits factor H co-factor activity

Protocol 1 (FIG. 15, panel A)—MaxiSorp plates were coated 3 hr at RT with 3 µg/ml C3b (PUR13420) in PBS (20 µl/well). The plates were washed 6× with 100 µl PBS 0.1% Tween (PBST) (BioTek EL405 washer), and blocked 2 hrs at RT with 4% BSA/0.05% Tween/PBS. The plates were incubated 30 min @RT with shaking blocking Abs, 20 µl followed by incubation 1 hr at RT with 0.33 µM fH (CompTech) and addition of 10 µl 1 µM fH. The plates were washed 6× with PBST in plate washer (BioTek EL405), incubated 30 min with 1:7000 donkey-anti-mouse IgG (H+L)—HRPO (Jackson), and washed 6× with PB ST in plate washer (BioTek EL405). Development was carried out with 20 µl TMB substrate. Reaction was stopped with 10 µl 2N sulfuric acid, and plates read at 450 nm Protocol 2 (FIG. 15, panel B)—All dilutions were in GVB++ (1 mM MgCl, 0.15 mM CaCl). Add in an eppendorf tube 10 µl 1.6 uM C3b (final 0.4 uM C3b). Add 10 µl anti-C3b Fab, control Fab or CR1. Incubate 20 min at RT. Add 10 µl 0.08 uM fI (final 20 nM fI). Incubate 60 min at 37 C. Add 40 µl Laemmeli's buffer+2-bME, boil 3 min. Run on 8% Invitrogen gel, 25 µl/well, 125 mV 1.5 hours. Wash gel 3×5 min $H_2O$, Stain 60 min at RT with rocking with Simply Blue (Invitrogen). Wash 3×5 min $ddH_2O$. Wash O/N with $ddH_2O$ in big baking dish on rocker, cover with plastic. Reagents: C3b PUR13240, fI from Complement Technologies, fH from Complement Technologies, GVB++ from BioWhittaker.

As described above, plates were coated with C3b. Factor H was added in the presence of increasing concentrations of control Fab or S77. Binding of factor H to C3b was determined using an anti factor H antibody and a secondary HRPO-conjugated anti mouse antibody. Color was developed with TMB (KPL), stopped in 2N $H_2SO_4$ and absorbance read at 450 nm The results are shown in FIG. 16, panel A.

Co-factor activity for factor I-mediated cleavage of C3b was measured by incubating 0.8 µM C3b and 80 nM factor I with 80 nM factor H or varying concentrations of S77 in 30 ml GVB. The mixture was incubated for 60 min at 37° C. and the samples analyzed by gel-electrophoresis as described for the C3 convertase assay. The results are shown in FIG. 16, panel B.

Figure 16:
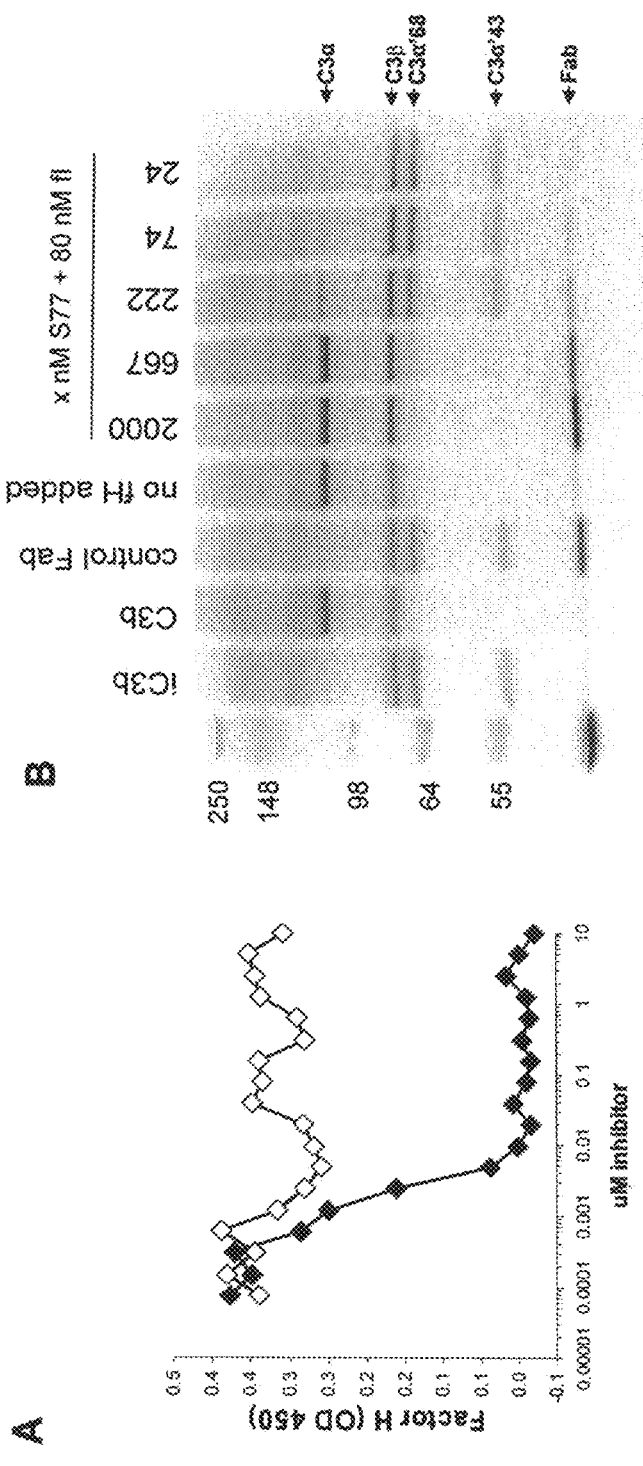
FIG. 16. S77 inhibits factor H binding to C3b and inhibits factor H co-factor activity.

As shown in FIG. 16, antibody S77 inhibits factor H binding to C3b and also inhibits factor H co-factor activity.

EXAMPLE 10

S77 inhibits CR1 binding to C3b

Protocol—Coat MaxiSorp plate o/n at 4 C with 3 μg/ml C3b (PUR13420) in PBS (100 μl/well). Wash 3× with 100 μl PBS 0.1% Tween (PBST) (BioTek EL405 washer). Block 2 hrs at RT with 4% BSA/0.1% Tween/PBS. Incubate 30 min at RT with shaking blocking Abs, 20 μl. Incubate 1 hr at RT with 50 nM CR1LHR-AC. Wash 3× with PBST in plate washer (BioTek EL405). Incubate 45 min at RT with 1:10 mIgG1 anti-hCD35-FITC (Pharmingen) in PBST. Wash 3× with PBST in plate washer (BioTek EL405). Incubate 30 min with 1:7000 donkey anti-mouse IgG—HRPO (Jackson) Wash 6× with PBST in plate washer (BioTek EL405). Develop with 20 μl TMB substrate. Stop reaction with 10 μl 2N sulfuric acid. Read plate at 450 nm.

Figure 17:
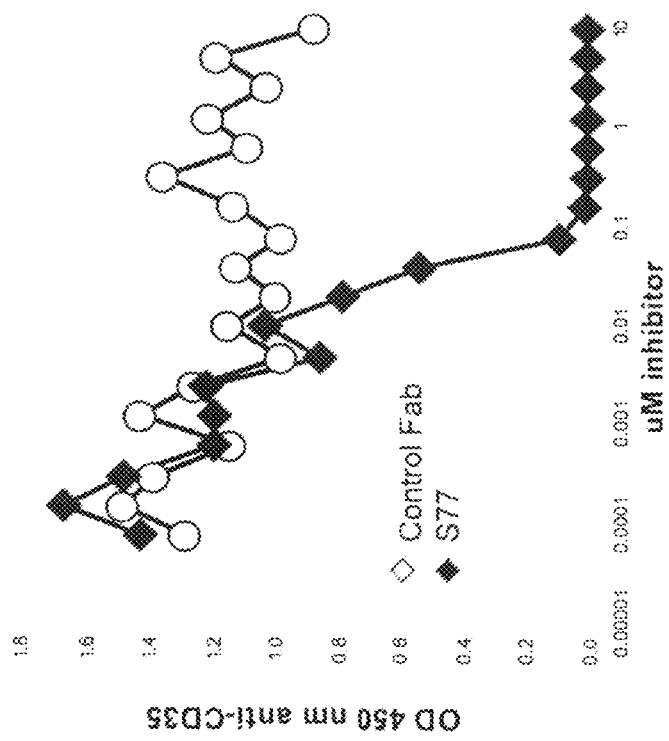
FIG. 17. S77 inhibits CR1 binding to C3b.

As shown in FIG. 17, antibody S77 inhibits CR1 binding to C3b.

EXAMPLE 11

Crystallization and data refinement

Hanging-drop experiments were performed using the vapor-diffusion method with 2 μl drops consisting of a 1:1 ratio of protein solution and reservoir solution. The protein solution contained the C3b:57714 complex at a concentration of 10 mg/ml in 25 mM Tris, 50 mM NaCl at pH 7.5 and the reservoir 10% PEG 4000, 0.2 M MgCl2 in 0.1 M Hepes at pH 7.2. Crystals appeared after two weeks. Crystals were incubated in reservoir solution supplemented with 20% glycerol prior to flash freezing. Data were collected from a single frozen crystal at the beam line 5.0.1 of the Advanced Light Source (Berkeley) and processed using the programs DENZO and SCALEPACK. Crystals belonged to space group C2 with cell parameters of a=216.4 Å, b=180.4 Å, c=154.6 Å and β=115.73 Å with 2 complexes, each composed of one C3b molecule bound to one Fab molecule in the asymmetric unit. The structure was solved by molecular replacement using the program Phaser and the coordinates of C3b, the constant domains, and the variable domains of a Fab fragment. The model was manually adjusted using program O and refinement was performed with program REFMAC using tight 2-fold non-crystallographic symmetry restraints. The R and $R_{free}$ of the refined model are 22.5% and 29.0% respectively.

Figure 3:
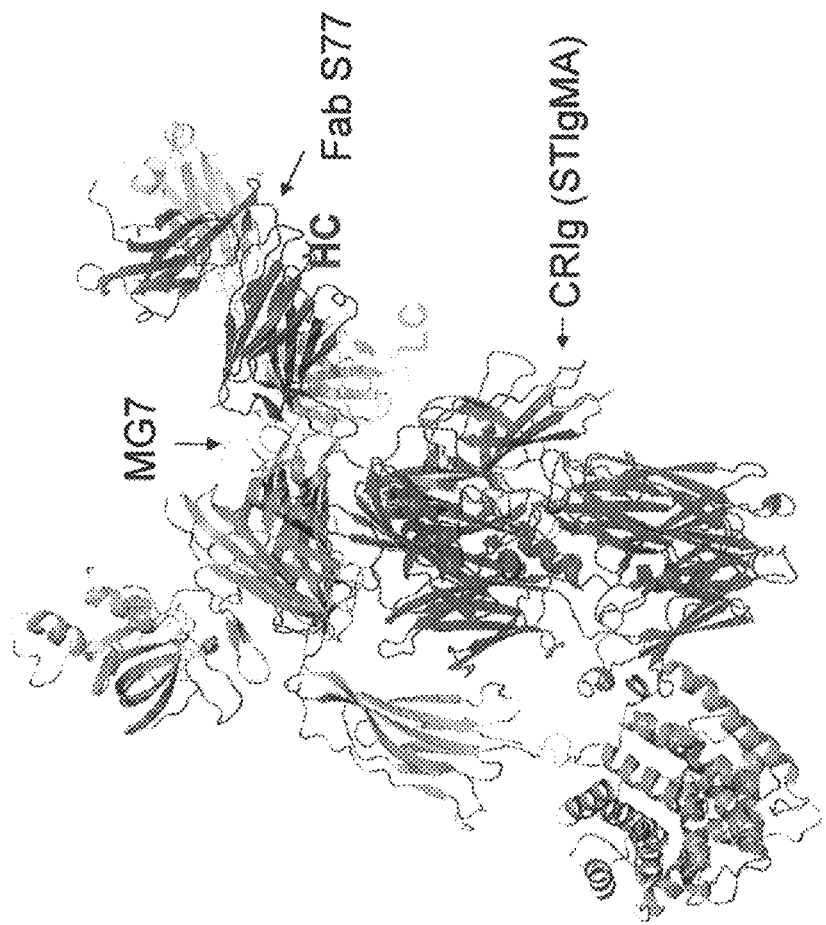
FIG. 3. Crystal structure of C3b in complex with antibody YW144.2.43.S77 (hereinafter briefly referred to as S77) Fab. The beta chain of C3b is indicated in green, the alpha chain is indicated in orange. The heavy chain (HC) and light chain (LC) of S77 are indicated in dark green and yellow, respectively. CRIg has been docked onto the C3b:Fab complex based on the C3b:CRIg co-crystal structure and is shown in magenta.

The crystal structure of C3b in complex with antibody S77 is sown in FIG. 3. FIG. 4I a close-up of the binding interaction of antibody S77 with C3b. Utilizing the crystallization data, the residues within the S77 Fab heavy chain sequence that are in close contact with C3b are shown in red.

In addition, FIG. 19 lists residues on C3b that are in contact with S77. FIG. 20 lists Fab S77 residues that are in contact with C3b.

Targeting C3b, a component central to complement activation, provides a powerful approach to inhibit the complement cascade at the level of both the C3 and C5 convertases. In the studies described in the Examples above, phage technology was employed to generate antibodies that selectively recognize C3b but not its pro-molecule C3. The crystal structure of C3b in complex with the Fab fragment of a specific antibody (S77) indicates that the antibody recognizes an epitope on the MG7 domain exposed following cleavage of C3 to C3b. S77 blocks binding of factor B and C5 to C3b, resulting in potent inhibition of the C3 and C5 convertases of the alternative, but not classical, complement pathway. In addition, S77 inhibits fH binding and cofactor activity, as well as CR1 binding to C3b, indicating that the binding site of S77 to the C3b MG7 domain is a hot-spot for regulation of complement activation. Together, the results of this study illustrate the molecular basis for complement activation and inhibition at the level of the C3 and C5 convertase of the alternative pathway, and demonstrate the utility of phage display, and other display technologies, to generate selective antibodies with promising therapeutic potential.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for inhibiting the alternative pathway of complement activation comprising administering to a subject in need an effective amount of an isolated anti-C3b antibody or antigen-binding fragment thereof that selectively binds to C3b and not to C3 and inhibits the binding of C5 to C3b, wherein said antibody comprises the heavy chain CDRH1, CDRH2 and CDRH3 sequences of SEQ ID NOS 2, 3, and 4, respectively, and the light chain CDRL1, CDRL2 and CDRL3 sequences of SEQ ID NOS 6, 7, and 8, respectively.

2. The method of claim 1 wherein said subject is a human.

3. The method of claim 1 wherein said antibody binds to an epitope including residues of the C3b epitope recognized by antibody S77.

4. The method of claim 1 wherein said antibody binds to the same epitope as antibody S77.

5. The method of claim 1 wherein said antibody competitively inhibits the binding of antibody S77.

6. The method of claim 1 wherein said antibody binds to a C3b epitope comprising residues that are in contact with antibody S77.

7. The method of claim 1 wherein said antibody comprises an antigen binding site comprising antibody S77 residues that are in contact with C3b.

8. The method of claim 1 wherein the antibody or antigen-binding fragment is human, humanized or chimeric.

9. The method of claim 1 wherein said antigen binding fragment is selected from the group consisting of Fab, Fab', F(ab')$_2$, scFv, (scFv)$_2$, dAb, a linear antibody, single-chain antibody molecule, minibody and diabody.

10. The method of claim 9 wherein said antigen binding fragment is a Fab, Fab', F(ab')$_2$, scFv, or (scFv)$_2$ fragment.

11. The method of claim 2 wherein said subject has a complement associated inflammatory disease.

12. The method of claim 2 wherein said complement-associated disorder is a complement-associated eye condition.

13. The method of claim 12 wherein the subject has age-related macular degeneration (AMD) or choroidal neovascularization (CNV).

14. The method of claim 1 wherein the antibody or antigen-binding fragment is antibody YW144.2.43S77 or a Fab fragment thereof.

* * * * *

SEQUENCE LISTING

```
<160> NUMBER OF SEQ ID NOS: 19

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      SS7 heavy chain region

<400> SEQUENCE: 1

Met Gly Trp Ser Cys Ile Ile Leu Phe Leu Val Ala Thr Ala Thr Gly
 1               5                   10                  15

Ala Tyr Ala Glu Val Gln Leu Val Glu Ser Gly Gly Gly Leu Val Gln
            20                  25                  30

Pro Gly Gly Ser Leu Arg Leu Ser Cys Ala Ala Ser
        35                  40
```

<210> SEQ ID NO 2
<211> LENGTH: 25
<212> TYPE: PRT
<213> ORGANISM: Artificial Sequence
<220> FEATURE:
<223> OTHER INFORMATION: Description of Artificial Sequence: Synthetic
      SS7 heavy chain region

<400> SEQUENCE: 2

Gly Phe Ser Phe Thr Ser Ser Val Ser Trp Val Arg Gln Ala Pro
 1               5                  10                  15

Gly Lys Gly Leu Glu Trp Val Gly Leu
                20                  25

<210> SEQ ID NO 3
<211> LENGTH: 48
<212> TYPE: PRT
<213> ORGANISM: Artificial Sequence
<220> FEATURE:
<223> OTHER INFORMATION: Description of Artificial Sequence: Synthetic
      SS7 heavy chain region

<400> SEQUENCE: 3

Ile Tyr Pro Tyr Asn Gly Phe Asn Tyr Tyr Ala Asp Ser Val Lys Gly
 1               5                  10                  15

Arg Phe Thr Ile Ser Ala Asp Thr Ser Lys Asn Thr Ala Tyr Leu Gln
                20                  25                  30

Met Asn Ser Leu Arg Ala Glu Asp Thr Ala Val Tyr Tyr Cys Ala Arg
            35                  40                  45

<210> SEQ ID NO 4
<211> LENGTH: 26
<212> TYPE: PRT
<213> ORGANISM: Artificial Sequence
<220> FEATURE:
<223> OTHER INFORMATION: Description of Artificial Sequence: Synthetic
      SS7 heavy chain region

<400> SEQUENCE: 4

Asn Ala Leu Tyr Gly Ser Gly Gly Tyr Tyr Ala Met Asp Tyr Trp Gly
 1               5                  10                  15

Gln Gly Thr Leu Val Thr Val Ser Ser Ala
                20                  25

<210> SEQ ID NO 5
<211> LENGTH: 42
<212> TYPE: PRT
<213> ORGANISM: Artificial Sequence
<220> FEATURE:
<223> OTHER INFORMATION: Description of Artificial Sequence: Synthetic
      S77 light chain region

<400> SEQUENCE: 5

Met Gly Trp Ser Cys Ile Ile Leu Phe Leu Val Ala Thr Ala Thr Gly
 1               5                  10                  15

Val His Ser Asp Ile Gln Met Thr Gln Ser Pro Ser Ser Leu Ser Ala
                20                  25                  30

Ser Val Gly Asp Arg Val Thr Ile Thr Cys
            35                  40

<210> SEQ ID NO 6
<211> LENGTH: 26
<212> TYPE: PRT
<213> ORGANISM: Artificial Sequence
<220> FEATURE:

```
<223> OTHER INFORMATION: Description of Artificial Sequence: Synthetic
      S77 light chain region

<400> SEQUENCE: 6

Arg Ala Ser Gln Asp Val Ser Thr Ala Val Ala Trp Tyr Gln Gln Lys
 1               5                  10                  15

Pro Gly Lys Ala Pro Lys Leu Leu Ile Tyr
            20                  25

<210> SEQ ID NO 7
<211> LENGTH: 39
<212> TYPE: PRT
<213> ORGANISM: Artificial Sequence
<220> FEATURE:
<223> OTHER INFORMATION: Description of Artificial Sequence: Synthetic
      S77 light chain region

<400> SEQUENCE: 7

Ser Ala Ser Phe Leu Tyr Ser Gly Val Pro Ser Arg Phe Ser Gly Ser
 1               5                  10                  15

Gly Ser Gly Thr Asp Phe Thr Leu Thr Ile Ser Ser Leu Gln Pro Glu
            20                  25                  30

Asp Phe Ala Thr Tyr Tyr Cys
        35

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence: Synthetic
      S77 light chain region

<400> SEQUENCE: 8

Gln Gln Ser Tyr Ala Thr Leu Pro Thr Phe Glu Gln Gly Thr Lys Val
 1               5                  10                  15

Glu Ile Lys

<210> SEQ ID NO 9
<211> LENGTH: 1641
<212> TYPE: PRT
<213> ORGANISM: Homo sapiens

<400> SEQUENCE: 9

Ser Pro Met Tyr Ser Ile Ile Thr Pro Asn Ile Leu Arg Leu Glu Ser
 1               5                  10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
```

```
                130                 135                 140
Ile Glu Asn Pro Glu Gly Ile Pro Val Lys Gln Asp Ser Leu Ser Ser
145                 150                 155                 160

Gln Asn Gln Leu Gly Val Leu Pro Leu Ser Trp Asp Ile Pro Glu Leu
                165                 170                 175

Val Asn Met Gly Gln Trp Lys Ile Arg Ala Tyr Tyr Glu Asn Ser Pro
                180                 185                 190

Gln Gln Val Phe Ser Thr Glu Phe Glu Val Lys Glu Tyr Val Leu Pro
                195                 200                 205

Ser Phe Glu Val Ile Val Glu Pro Thr Glu Lys Phe Tyr Tyr Ile Tyr
210                 215                 220

Asn Glu Lys Gly Leu Glu Val Thr Ile Thr Ala Arg Phe Leu Tyr Gly
225                 230                 235                 240

Lys Lys Val Glu Gly Thr Ala Phe Val Ile Phe Gly Ile Gln Asp Gly
                245                 250                 255

Glu Gln Arg Ile Ser Leu Pro Glu Ser Leu Lys Arg Ile Pro Ile Glu
                260                 265                 270

Asp Gly Ser Gly Glu Val Val Leu Ser Arg Lys Val Leu Leu Asp Gly
                275                 280                 285

Val Gln Asn Leu Arg Ala Glu Asp Leu Val Gly Lys Ser Leu Tyr Val
290                 295                 300

Ser Ala Thr Val Ile Leu His Ser Gly Ser Asp Met Val Gln Ala Glu
305                 310                 315                 320

Arg Ser Gly Ile Pro Ile Val Thr Ser Pro Tyr Gln Ile His Phe Thr
                325                 330                 335

Lys Thr Pro Lys Tyr Phe Lys Pro Gly Met Pro Phe Asp Leu Met Val
                340                 345                 350

Phe Val Thr Asn Pro Asp Gly Ser Pro Ala Tyr Arg Val Pro Ala Val
                355                 360                 365

Ala Val Gln Gly Glu Asp Thr Val Gln Ser Leu Thr Gln Gly Asp Gly
                370                 375                 380

Val Ala Lys Leu Ser Ile Asn Thr His Pro Ser Gln Lys Pro Leu Ser
385                 390                 395                 400

Ile Thr Val Arg Thr Lys Lys Gln Glu Leu Ser Glu Ala Glu Gln Ala
                405                 410                 415

Thr Arg Thr Met Gln Ala Leu Pro Tyr Ser Thr Val Gly Asn Ser Asn
                420                 425                 430

Asn Tyr Leu His Leu Ser Val Leu Arg Thr Glu Leu Arg Pro Gly Glu
                435                 440                 445

Thr Leu Asn Val Asn Phe Leu Leu Arg Met Asp Arg Ala His Glu Ala
450                 455                 460

Lys Ile Arg Tyr Tyr Thr Tyr Leu Ile Met Asn Lys Gly Arg Leu Leu
465                 470                 475                 480

Lys Ala Gly Arg Gln Val Arg Glu Pro Gly Gln Asp Leu Val Val Leu
                485                 490                 495

Pro Leu Ser Ile Thr Thr Asp Phe Ile Pro Ser Phe Arg Leu Val Ala
                500                 505                 510

Tyr Tyr Thr Leu Ile Gly Ala Ser Gly Gln Arg Glu Val Val Ala Asp
                515                 520                 525

Ser Val Trp Val Asp Val Lys Asp Ser Cys Val Gly Ser Leu Val Val
                530                 535                 540

Lys Ser Gly Gln Ser Glu Asp Arg Gln Pro Val Pro Gly Gln Gln Met
545                 550                 555                 560
```

```
Thr Leu Lys Ile Glu Gly Asp His Gly Ala Arg Val Leu Val Ala
            565                 570                 575

Val Asp Lys Gly Val Phe Val Leu Asn Lys Lys Asn Lys Leu Thr Gln
                580                 585                 590

Ser Lys Ile Trp Asp Val Val Glu Lys Ala Asp Ile Gly Cys Thr Pro
            595                 600                 605

Gly Ser Gly Lys Asp Tyr Ala Gly Val Phe Ser Asp Ala Gly Leu Thr
            610                 615                 620

Phe Thr Ser Ser Ser Gly Gln Gln Thr Ala Gln Arg Ala Glu Leu Gln
625                 630                 635                 640

Cys Pro Gln Pro Ala Ala Arg Arg Arg Ser Val Gln Leu Thr Glu
            645                 650                 655

Lys Arg Met Asp Lys Val Gly Lys Tyr Pro Lys Glu Leu Arg Lys Cys
            660                 665                 670

Cys Asp Gly Met Arg Glu Asn Pro Met Arg Phe Ser Cys Gln Arg
        675                 680                 685

Arg Thr Arg Phe Ile Ser Leu Gly Glu Ala Cys Lys Lys Val Phe Leu
    690                 695                 700

Asp Cys Cys Asn Tyr Ile Thr Glu Leu Arg Arg Gln His Ala Arg Ala
705                 710                 715                 720

Ser His Leu Gly Leu Ala Arg Ser Asn Leu Asp Glu Asp Ile Ile Ala
                725                 730                 735

Glu Glu Asn Ile Val Ser Arg Ser Glu Phe Pro Glu Ser Trp Leu Trp
                740                 745                 750

Asn Val Glu Asp Leu Lys Glu Pro Pro Lys Asn Gly Ile Ser Thr Lys
            755                 760                 765

Leu Asn Asn Ile Phe Leu Lys Asp Ser Ile Thr Thr Trp Glu Ile Leu
770                 775                 780

Ala Val Ser Met Ser Asp Lys Lys Gly Ile Cys Val Ala Asp Pro Phe
785                 790                 795                 800

Glu Val Thr Val Met Gln Asp Phe Phe Ile Asp Leu Arg Leu Pro Tyr
                805                 810                 815

Ser Val Val Arg Asn Glu Gln Val Glu Ile Arg Ala Val Leu Tyr Asn
            820                 825                 830

Tyr Arg Gln Asn Gln Glu Leu Lys Val Arg Val Glu Leu Leu His Asn
        835                 840                 845

Pro Ala Phe Cys Ser Leu Ala Thr Thr Lys Arg Arg His Gln Gln Thr
850                 855                 860

Val Thr Ile Pro Pro Lys Ser Ser Leu Ser Val Pro Tyr Val Ile Val
865                 870                 875                 880

Pro Leu Lys Thr Gly Leu Gln Glu Val Glu Val Lys Ala Ala Val Tyr
                885                 890                 895

His His Phe Ile Ser Asp Gly Val Arg Lys Ser Leu Lys Val Val Pro
            900                 905                 910

Glu Gly Ile Arg Met Asn Lys Thr Val Ala Val Arg Thr Leu Asp Pro
        915                 920                 925

Glu Arg Leu Gly Arg Glu Gly Val Gln Lys Glu Asp Ile Pro Pro Ala
    930                 935                 940

Asp Leu Ser Asp Gln Val Pro Asp Thr Glu Ser Glu Thr Arg Ile Leu
945                 950                 955                 960

Leu Gln Gly Thr Pro Val Ala Gln Met Thr Glu Asp Ala Val Asp Ala
                965                 970                 975

Glu Arg Leu Lys His Leu Ile Val Thr Pro Ser Gly Cys Gly Glu Gln
            980                 985                 990
```

-continued

```
Asn Met Ile Gly Met Thr Pro Thr Val Ile Ala Val His Tyr Leu Asp
        995                 1000                1005

Glu Thr Glu Gln Trp Glu Lys Phe Gly Leu Glu Lys Arg Gln Gly Ala
1010                1015                1020

Leu Glu Leu Ile Lys Lys Gly Tyr Thr Gln Gln Leu Ala Phe Arg Gln
1025                1030                1035                1040

Pro Ser Ser Ala Phe Ala Ala Phe Val Lys Arg Ala Pro Ser Thr Trp
            1045                1050                1055

Leu Thr Ala Tyr Val Val Lys Val Phe Ser Leu Ala Val Asn Leu Ile
        1060                1065                1070

Ala Ile Asp Ser Gln Val Leu Cys Gly Ala Val Lys Trp Leu Ile Leu
        1075                1080                1085

Glu Lys Gln Lys Pro Asp Gly Val Phe Gln Glu Asp Ala Pro Val Ile
        1090                1095                1100

His Gln Glu Met Ile Gly Gly Leu Arg Asn Asn Asn Glu Lys Asp Met
1105                1110                1115                1120

Ala Leu Thr Ala Phe Val Leu Ile Ser Leu Gln Glu Ala Lys Asp Ile
            1125                1130                1135

Cys Glu Glu Gln Val Asn Ser Leu Pro Gly Ser Ile Thr Lys Ala Gly
        1140                1145                1150

Asp Phe Leu Glu Ala Asn Tyr Met Asn Leu Gln Arg Ser Tyr Thr Val
        1155                1160                1165

Ala Ile Ala Gly Tyr Ala Leu Ala Gln Met Gly Arg Leu Lys Gly Pro
        1170                1175                1180

Leu Leu Asn Lys Phe Leu Thr Thr Ala Lys Asp Lys Asn Arg Trp Glu
1185                1190                1195                1200

Asp Pro Gly Lys Gln Leu Tyr Asn Val Glu Ala Thr Ser Tyr Ala Leu
            1205                1210                1215

Leu Ala Leu Leu Gln Leu Lys Asp Phe Asp Phe Val Pro Pro Val Val
        1220                1225                1230

Arg Trp Leu Asn Glu Gln Arg Tyr Tyr Gly Gly Gly Tyr Gly Ser Thr
        1235                1240                1245

Gln Ala Thr Phe Met Val Phe Gln Ala Leu Ala Gln Tyr Gln Lys Asp
1250                1255                1260

Ala Pro Asp His Gln Glu Leu Asn Leu Asp Val Ser Leu Gln Leu Pro
1265                1270                1275                1280

Ser Arg Ser Ser Lys Ile Thr His Arg Ile His Trp Glu Ser Ala Ser
            1285                1290                1295

Leu Leu Arg Ser Glu Glu Thr Lys Glu Asn Glu Gly Phe Thr Val Thr
        1300                1305                1310

Ala Glu Gly Lys Gly Gln Gly Thr Leu Ser Val Val Thr Met Tyr His
        1315                1320                1325

Ala Lys Ala Lys Asp Gln Leu Thr Cys Asn Lys Phe Asp Leu Lys Val
        1330                1335                1340

Thr Ile Lys Pro Ala Pro Glu Thr Glu Lys Arg Pro Gln Asp Ala Lys
1345                1350                1355                1360

Asn Thr Met Ile Leu Glu Ile Cys Thr Arg Tyr Arg Gly Asp Gln Asp
            1365                1370                1375

Ala Thr Met Ser Ile Leu Asp Ile Ser Met Met Thr Gly Phe Ala Pro
        1380                1385                1390

Asp Thr Asp Asp Leu Lys Gln Leu Ala Asn Gly Val Asp Arg Tyr Ile
        1395                1400                1405

Ser Lys Tyr Glu Leu Asp Lys Ala Phe Ser Asp Arg Asn Thr Leu Ile
```

```
          1410                1415                1420
Ile Tyr Leu Asp Lys Val Ser His Ser Glu Asp Cys Leu Ala Phe
1425                1430                1435                1440

Lys Val His Gln Tyr Phe Asn Val Glu Leu Ile Gln Pro Gly Ala Val
                1445                1450                1455

Lys Val Tyr Ala Tyr Tyr Asn Leu Glu Glu Ser Cys Thr Arg Phe Tyr
                1460                1465                1470

His Pro Glu Lys Glu Asp Gly Lys Leu Asn Lys Leu Cys Arg Asp Glu
                1475                1480                1485

Leu Cys Arg Cys Ala Glu Glu Cys Phe Ile Gln Lys Ser Asp Asp Lys
                1490                1495                1500

Val Thr Leu Glu Glu Arg Leu Asp Lys Ala Cys Glu Pro Gly Val Asp
1505                1510                1515                1520

Tyr Val Tyr Lys Thr Arg Leu Val Lys Val Gln Leu Ser Asn Asp Phe
                1525                1530                1535

Asp Glu Tyr Ile Met Ala Ile Glu Gln Thr Ile Lys Ser Gly Ser Asp
                1540                1545                1550

Glu Val Gln Val Gly Gln Gln Arg Thr Phe Ile Ser Pro Ile Lys Cys
                1555                1560                1565

Arg Glu Ala Leu Lys Leu Glu Glu Lys Lys His Tyr Leu Met Trp Gly
                1570                1575                1580

Leu Ser Ser Asp Phe Trp Gly Glu Lys Pro Asn Leu Ser Tyr Ile Ile
1585                1590                1595                1600

Gly Lys Asp Thr Trp Val Glu His Trp Pro Glu Glu Asp Glu Cys Gln
                1605                1610                1615

Asp Glu Glu Asn Gln Lys Gln Cys Gln Asp Leu Gly Ala Phe Thr Glu
                1620                1625                1630

Ser Met Val Val Phe Gly Cys Pro Asn
                1635                1640

<210> SEQ ID NO 10
<211> LENGTH: 1639
<212> TYPE: PRT
<213> ORGANISM: Mus musculus

<400> SEQUENCE: 10

Ile Pro Met Tyr Ser Ile Ile Thr Pro Asn Val Leu Arg Leu Glu Ser
 1               5                  10                  15

Glu Glu Thr Ile Val Leu Glu Ala His Asp Ala Gln Gly Asp Ile Pro
                20                  25                  30

Val Thr Val Thr Val Gln Asp Phe Leu Lys Arg Gln Val Leu Thr Ser
                35                  40                  45

Glu Lys Thr Val Leu Thr Gly Ala Ser Gly His Leu Arg Ser Val Ser
        50                  55                  60

Ile Lys Ile Pro Ala Ser Lys Glu Phe Asn Ser Asp Lys Glu Gly His
65                  70                  75                  80

Lys Tyr Val Thr Val Ala Asn Phe Gly Glu Thr Val Val Glu Lys
                85                  90                  95

Ala Val Met Val Ser Phe Gln Ser Gly Tyr Leu Phe Ile Gln Thr Asp
                100                 105                 110

Lys Thr Ile Tyr Thr Pro Gly Ser Thr Val Leu Tyr Arg Ile Phe Thr
                115                 120                 125

Val Asp Asn Asn Leu Leu Pro Val Gly Lys Thr Val Val Ile Leu Ile
                130                 135                 140

Glu Thr Pro Asp Gly Ile Pro Val Lys Arg Asp Ile Leu Ser Ser Asn
```

-continued

```
            145                 150                 155                 160
Asn Gln His Gly Ile Leu Pro Leu Ser Trp Asn Ile Pro Glu Leu Val
                165                 170                 175
Asn Met Gly Gln Trp Lys Ile Arg Ala Phe Tyr Glu His Ala Pro Lys
                180                 185                 190
Gln Ile Phe Ser Ala Glu Phe Glu Val Lys Glu Tyr Val Leu Pro Ser
                195                 200                 205
Phe Glu Val Arg Val Glu Pro Thr Glu Thr Phe Tyr Tyr Ile Asp Asp
                210                 215                 220
Pro Asn Gly Leu Glu Val Ser Ile Ile Ala Lys Phe Leu Tyr Gly Lys
225                 230                 235                 240
Asn Val Asp Gly Thr Ala Phe Val Ile Phe Gly Val Gln Asp Gly Asp
                245                 250                 255
Lys Lys Ile Ser Leu Ala His Ser Leu Thr Arg Val Val Ile Glu Asp
                260                 265                 270
Gly Val Gly Asp Ala Val Leu Thr Arg Lys Val Leu Met Glu Gly Val
                275                 280                 285
Arg Pro Ser Asn Ala Asp Ala Leu Val Gly Lys Ser Leu Tyr Val Ser
                290                 295                 300
Val Thr Val Ile Leu His Ser Gly Ser Asp Met Val Glu Ala Glu Arg
305                 310                 315                 320
Ser Gly Ile Pro Ile Val Thr Ser Pro Tyr Gln Ile His Phe Thr Lys
                325                 330                 335
Thr Pro Lys Phe Phe Lys Pro Ala Met Pro Phe Asp Leu Met Val Phe
                340                 345                 350
Val Thr Asn Pro Asp Gly Ser Pro Ala Ser Lys Val Leu Val Val Thr
                355                 360                 365
Gln Gly Ser Asn Ala Lys Ala Leu Thr Gln Asp Asp Gly Val Ala Lys
                370                 375                 380
Leu Ser Ile Asn Thr Pro Asn Ser Arg Gln Pro Leu Thr Ile Thr Val
385                 390                 395                 400
Arg Thr Lys Lys Asp Thr Leu Pro Glu Ser Arg Gln Ala Thr Lys Thr
                405                 410                 415
Met Glu Ala His Pro Tyr Ser Thr Met His Asn Ser Asn Asn Tyr Leu
                420                 425                 430
His Leu Ser Val Ser Arg Met Glu Leu Lys Pro Gly Asp Asn Leu Asn
                435                 440                 445
Val Asn Phe His Leu Arg Thr Asp Pro Gly His Glu Ala Lys Ile Arg
                450                 455                 460
Tyr Tyr Thr Tyr Leu Val Met Asn Lys Gly Lys Leu Leu Lys Ala Gly
465                 470                 475                 480
Arg Gln Val Arg Glu Pro Gly Gln Asp Leu Val Val Leu Ser Leu Pro
                485                 490                 495
Ile Thr Pro Glu Phe Ile Pro Ser Phe Arg Leu Val Ala Tyr Tyr Thr
                500                 505                 510
Leu Ile Gly Ala Ser Gly Gln Arg Glu Val Val Ala Asp Ser Val Trp
                515                 520                 525
Val Asp Val Lys Asp Ser Cys Ile Gly Thr Leu Val Val Lys Gly Asp
                530                 535                 540
Pro Arg Asp Asn His Leu Ala Pro Gly Gln Gln Thr Thr Leu Arg Ile
545                 550                 555                 560
Glu Gly Asn Gln Gly Ala Arg Val Gly Leu Val Ala Val Asp Lys Gly
                565                 570                 575
```

-continued

```
Val Phe Val Leu Asn Lys Lys Asn Lys Leu Thr Gln Ser Lys Ile Trp
                580                 585                 590

Asp Val Val Glu Lys Ala Asp Ile Gly Cys Thr Pro Gly Ser Gly Lys
            595                 600                 605

Asn Tyr Ala Gly Val Phe Met Asp Ala Gly Leu Ala Phe Lys Thr Ser
610                 615                 620

Gln Gly Leu Gln Thr Glu Gln Arg Ala Asp Leu Glu Cys Thr Lys Pro
625                 630                 635                 640

Ala Ala Arg Arg Arg Ser Val Gln Leu Met Glu Arg Arg Met Asp
                645                 650                 655

Lys Ala Gly Gln Tyr Thr Asp Lys Gly Leu Arg Lys Cys Cys Glu Asp
            660                 665                 670

Gly Met Arg Asp Ile Pro Met Arg Tyr Ser Cys Gln Arg Arg Ala Arg
            675                 680                 685

Leu Ile Thr Gln Gly Glu Asn Cys Ile Lys Ala Phe Ile Asp Cys Cys
            690                 695                 700

Asn His Ile Thr Lys Leu Arg Glu Gln His Arg Arg Asp His Val Leu
705                 710                 715                 720

Gly Leu Ala Arg Ser Glu Leu Glu Glu Asp Ile Ile Pro Glu Glu Asp
                725                 730                 735

Ile Ile Ser Arg Ser His Phe Pro Gln Ser Trp Leu Trp Thr Ile Glu
            740                 745                 750

Glu Leu Lys Glu Pro Glu Lys Asn Gly Ile Ser Thr Lys Val Met Asn
            755                 760                 765

Ile Phe Leu Lys Asp Ser Ile Thr Thr Trp Gln Ile Leu Ala Val Ser
            770                 775                 780

Leu Ser Asp Lys Lys Gly Ile Cys Val Ala Asp Pro Tyr Glu Ile Arg
785                 790                 795                 800

Val Met Gln Asp Phe Phe Ile Asp Leu Arg Leu Pro Tyr Ser Val Val
                805                 810                 815

Arg Asn Glu Gln Val Glu Ile Arg Ala Val Leu Phe Asn Tyr Arg Glu
            820                 825                 830

Gln Glu Glu Leu Lys Val Arg Val Glu Leu Leu His Asn Pro Ala Phe
            835                 840                 845

Cys Ser Met Ala Thr Ala Lys Asn Arg Tyr Phe Gln Thr Ile Lys Ile
850                 855                 860

Pro Pro Lys Ser Ser Val Ala Val Pro Tyr Val Ile Val Pro Leu Lys
865                 870                 875                 880

Ile Gly Gln Gln Glu Val Glu Val Lys Ala Ala Val Phe Asn His Phe
                885                 890                 895

Ile Ser Asp Gly Val Lys Lys Thr Leu Lys Val Val Pro Glu Gly Met
            900                 905                 910

Arg Ile Asn Lys Thr Val Ala Ile His Thr Leu Asp Pro Glu Lys Leu
            915                 920                 925

Gly Gln Gly Gly Val Gln Lys Val Asp Val Pro Ala Ala Asp Leu Ser
            930                 935                 940

Asp Gln Val Pro Asp Thr Asp Ser Glu Thr Arg Ile Ile Leu Gln Gly
945                 950                 955                 960

Ser Pro Val Val Gln Met Ala Glu Asp Ala Val Asp Gly Glu Arg Leu
                965                 970                 975

Lys His Leu Ile Val Thr Pro Ala Gly Cys Gly Glu Gln Asn Met Ile
            980                 985                 990

Gly Met Thr Pro Thr Val Ile Ala Val His Tyr Leu Asp Gln Thr Glu
            995                 1000                1005
```

```
Gln Trp Glu Lys Phe Gly Ile Glu Lys Arg Gln Glu Ala Leu Glu Leu
    1010                1015                1020

Ile Lys Lys Gly Tyr Thr Gln Gln Leu Ala Phe Lys Gln Pro Ser Ser
1025                1030                1035                1040

Ala Tyr Ala Ala Phe Asn Asn Arg Pro Pro Ser Thr Trp Leu Thr Ala
            1045                1050                1055

Tyr Val Val Lys Val Phe Ser Leu Ala Ala Asn Leu Ile Ala Ile Asp
        1060                1065                1070

Ser His Val Leu Cys Gly Ala Val Lys Trp Leu Ile Leu Glu Lys Gln
    1075                1080                1085

Lys Pro Asp Gly Val Phe Gln Glu Asp Gly Pro Val Ile His Gln Glu
1090                1095                1100

Met Ile Gly Gly Phe Arg Asn Ala Lys Glu Ala Asp Val Ser Leu Thr
1105                1110                1115                1120

Ala Phe Val Leu Ile Ala Leu Gln Glu Ala Arg Asp Ile Cys Glu Gly
            1125                1130                1135

Gln Val Asn Ser Leu Pro Gly Ser Ile Asn Lys Ala Gly Glu Tyr Ile
        1140                1145                1150

Glu Ala Ser Tyr Met Asn Leu Gln Arg Pro Tyr Thr Val Ala Ile Ala
    1155                1160                1165

Gly Tyr Ala Leu Ala Leu Met Asn Lys Leu Glu Glu Pro Tyr Leu Gly
    1170                1175                1180

Lys Phe Leu Asn Thr Ala Lys Asp Arg Asn Arg Trp Glu Glu Pro Asp
1185                1190                1195                1200

Gln Gln Leu Tyr Asn Val Glu Ala Thr Ser Tyr Ala Leu Leu Ala Leu
        1205                1210                1215

Leu Leu Leu Lys Asp Phe Asp Ser Val Pro Pro Val Val Arg Trp Leu
        1220                1225                1230

Asn Glu Gln Arg Tyr Tyr Gly Gly Gly Tyr Gly Ser Thr Gln Ala Thr
    1235                1240                1245

Phe Met Val Phe Gln Ala Leu Ala Gln Tyr Gln Thr Asp Val Pro Asp
    1250                1255                1260

His Lys Asp Leu Asn Met Asp Val Ser Phe His Leu Pro Ser Arg Ser
1265                1270                1275                1280

Ser Ala Thr Thr Phe Arg Leu Leu Trp Glu Asn Gly Asn Leu Leu Arg
            1285                1290                1295

Ser Glu Glu Thr Lys Gln Asn Glu Ala Phe Ser Leu Thr Ala Lys Gly
        1300                1305                1310

Lys Gly Arg Gly Thr Leu Ser Val Val Ala Val Tyr His Ala Lys Leu
        1315                1320                1325

Lys Ser Lys Val Thr Cys Lys Lys Phe Asp Leu Arg Val Ser Ile Arg
    1330                1335                1340

Pro Ala Pro Glu Thr Ala Lys Lys Pro Glu Glu Ala Lys Asn Thr Met
1345                1350                1355                1360

Phe Leu Glu Ile Cys Thr Lys Tyr Leu Gly Asp Val Asp Ala Thr Met
            1365                1370                1375

Ser Ile Leu Asp Ile Ser Met Met Thr Gly Phe Ala Pro Asp Thr Lys
        1380                1385                1390

Asp Leu Glu Leu Leu Ala Ser Gly Val Asp Arg Tyr Ile Ser Lys Tyr
    1395                1400                1405

Glu Met Asn Lys Ala Phe Ser Asn Lys Asn Thr Leu Ile Ile Tyr Leu
    1410                1415                1420

Glu Lys Ile Ser His Thr Glu Glu Asp Cys Leu Thr Phe Lys Val His
```

```
1425                1430                1435                1440

Gln Tyr Phe Asn Val Gly Leu Ile Gln Pro Gly Ser Val Lys Val Tyr
                1445                1450                1455

Ser Tyr Tyr Asn Leu Glu Glu Ser Cys Thr Arg Phe Tyr His Pro Glu
            1460                1465                1470

Lys Asp Asp Gly Met Leu Ser Lys Leu Cys His Ser Glu Met Cys Arg
        1475                1480                1485

Cys Ala Glu Glu Asn Cys Phe Met Gln Gln Ser Gln Glu Lys Ile Asn
    1490                1495                1500

Leu Asn Val Arg Leu Asp Lys Ala Cys Glu Pro Gly Val Asp Tyr Val
1505                1510                1515                1520

Tyr Lys Thr Glu Leu Thr Asn Ile Lys Leu Leu Asp Asp Phe Asp Glu
                1525                1530                1535

Tyr Thr Met Thr Ile Gln Gln Val Ile Lys Ser Gly Ser Asp Glu Val
            1540                1545                1550

Gln Ala Gly Gln Gln Arg Lys Phe Ile Ser His Ile Lys Cys Arg Asn
        1555                1560                1565

Ala Leu Lys Leu Gln Lys Gly Lys Lys Tyr Leu Met Trp Gly Leu Ser
    1570                1575                1580

Ser Asp Leu Trp Gly Glu Lys Pro Asn Thr Ser Tyr Ile Ile Gly Lys
1585                1590                1595                1600

Asp Thr Trp Val Glu His Trp Pro Glu Ala Glu Glu Cys Gln Asp Gln
                1605                1610                1615

Lys Tyr Gln Lys Gln Cys Glu Glu Leu Gly Ala Phe Thr Glu Ser Met
            1620                1625                1630

Val Val Tyr Gly Cys Pro Asn
        1635

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ala Ser Gln Ser Ile Ser Ser Tyr Leu Ala
  1               5                  10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Ala Ser Ser Arg Ala Ser
  1               5

<210> SEQ ID NO 13
<211> LENGTH: 214
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
  1               5                  10                  15
```

-continued

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
210

<210> SEQ ID NO 14
<211> LENGTH: 449
<212> TYPE: PRT
<213> ORGANISM: Homo sapiens

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
        100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Asp
        195                 200                 205

Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gln Asn Gln Glu Leu Lys
  1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr His His Phe Ile
  1               5
```

```
<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Ser Ser Ser
 1

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Asn Ala Leu Tyr Gly Ser Gly Gly Tyr
 1               5                   10

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 19

His His His His His His
 1               5
```